(12) United States Patent
Tarumi et al.

(10) Patent No.: US 11,164,675 B2
(45) Date of Patent: Nov. 2, 2021

(54) TREATMENT SELECTION SUPPORT SYSTEM AND METHOD

(71) Applicant: Hitachi, Ltd., Tokyo (JP)

(72) Inventors: Shinji Tarumi, Tokyo (JP); Wataru Takeuchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 490 days.

(21) Appl. No.: 16/185,501

(22) Filed: Nov. 9, 2018

(65) Prior Publication Data

US 2019/0156956 A1 May 23, 2019

(30) Foreign Application Priority Data

Nov. 21, 2017 (JP) .............................. JP2017-223492

(51) Int. Cl.
| | |
|---|---|
| *G16H 50/20* | (2018.01) |
| *G16H 50/50* | (2018.01) |
| *A61B 5/00* | (2006.01) |
| *A61B 5/145* | (2006.01) |

(52) U.S. Cl.
CPC ............ *G16H 50/50* (2018.01); *G16H 50/20* (2018.01); *A61B 5/14532* (2013.01); *A61B 5/4848* (2013.01); *A61B 5/7282* (2013.01)

(58) Field of Classification Search
CPC ........... A61P 3/10; G16H 50/20; G16H 50/50
See application file for complete search history.

(56) References Cited

U.S. PATENT DOCUMENTS

| | | | |
|---|---|---|---|
| 2009/0137499 A1* | 5/2009 | Honda | ................. A61K 9/2018 514/27 |
| 2013/0268547 A1 | 10/2013 | Boroczky et al. | |
| 2014/0095202 A1 | 4/2014 | Kudou et al. | |

(Continued)

FOREIGN PATENT DOCUMENTS

| | | |
|---|---|---|
| JP | 2014-071592 A | 4/2014 |
| WO | 2012/080906 A1 | 6/2012 |

*Primary Examiner* — Reginald R Reyes
(74) *Attorney, Agent, or Firm* — Procopio, Cory, Hargreaves & Savitch LLP

(57) ABSTRACT

It is provided a treatment selection support system comprising: a target achievement determination module configured to create target achievement determination information; a blood sugar controllability estimation module configured to create blood sugar controllability information; an achievement level prediction model creation module configured to create an achievement level prediction model; an appropriateness level calculation model creation module configured to create an appropriateness level calculation model for calculating an appropriateness level of a blood sugar control means based on formatted information, the target achievement determination information, and the blood sugar controllability information; an achievement level prediction module configured to use the achievement level prediction model; an appropriateness level calculation module configured to use the appropriateness level calculation model; and a blood sugar control means suggestion module configured to provide information on the blood sugar control means appropriate for the patient based on the predicted achievement level and the calculated appropriateness level.

11 Claims, 14 Drawing Sheets

(56) References Cited

U.S. PATENT DOCUMENTS

2014/0105839 A1* 4/2014 Deliencourt-Godefroy ................ C07C 43/247
424/62
2019/0043501 A1* 2/2019 Ramaci .................. G16H 40/67

* cited by examiner

PATIENT BASIC INFORMATION 201

| PATIENT ID 202 | GENDER 203 | AGE 204 | ... |
|---|---|---|---|
| P0001 | MALE | 60 | |
| P0002 | FEMALE | 73 | |
| P0003 | MALE | 88 | |
| P0004 | FEMALE | 58 | |
| ... | ... | ... | |

*Fig. 2*

EXAMINATION INFORMATION 1701

| PATIENT ID 202 | DIAGNOSIS-OR-TREATMENT ID 1702 | DATE 1703 | ITEM ID 1704 | VALUE 1705 | UNIT 1706 | ... |
|---|---|---|---|---|---|---|
| P0001 | V0001 | 20171007 | I0001 | 8.1 | % | |
| P0001 | V0002 | 20171106 | I0001 | 7.7 | % | |
| P0001 | V0003 | 20171203 | I0001 | 6.8 | % | |
| P0002 | V0001 | 20171031 | I0003 | 70 | kg | |
| ... | ... | ... | ... | ... | ... | |

*Fig. 3*

DISEASE INFORMATION 1801

| PATIENT ID 202 | DIAGNOSIS-OR-TREATMENT ID 1702 | DATE 1703 | DISEASE ID 1802 | ... |
|---|---|---|---|---|
| P0001 | V0001 | 20171007 | D0002 | |
| P0001 | V0002 | 20171106 | D0002 | |
| P0001 | V0003 | 20171203 | D0002 | |
| P0002 | V0001 | 20171031 | D0003 | |
| ... | ... | ... | ... | |

*Fig. 4*

| PATIENT ID (202) | DIAGNOSIS-OR-TREATMENT ID (1702) | DATE (1703) | DRUG ID (1902) | PRESCRIBED AMOUNT (1903) | UNIT (1904) | ... (1901) |
|---|---|---|---|---|---|---|
| P0001 | V0001 | 20171007 | M0001 | 500 | mg | |
| P0001 | V0002 | 20171106 | M0001 | 1000 | mg | |
| P0001 | V0002 | 20171106 | M0002 | 3 | mg | |
| ... | ... | ... | ... | ... | ... | |

BLOOD SUGAR CONTROL MEANS IMPLEMENTATION INFORMATION

*Fig. 5*

| TARGET ID (2002) | ITEM ID (1704) | TARGET VALUE (2003) | TARGET PERIOD (2004) | TARGET PERIOD UNIT (2005) | ... (2001) |
|---|---|---|---|---|---|
| G0001 | I0001 | 8.0 | 30 | DAY | |
| G0002 | I0001 | 7.0 | 30 | DAY | |
| ... | | ... | ... | | |

BLOOD SUGAR CONTROL TARGET INFORMATION

*Fig. 6*

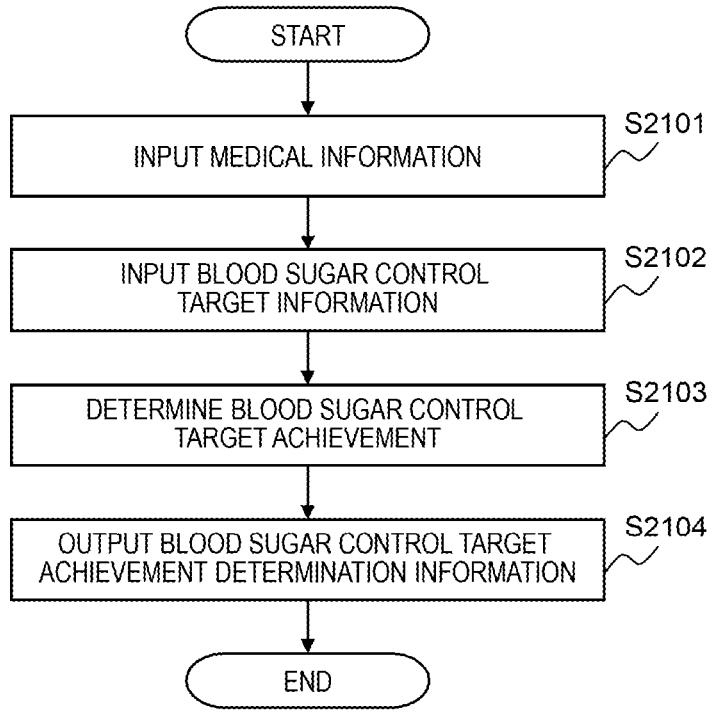

FORMATTED INFORMATION 2303

MEDICAL INFORMATION 2302

| PATIENT ID | DIAGNOSIS-OR-TREATMENT ID | GENDER | AGE | ... | HbA1c | ... | BLOOD SUGAR CONTROL MEANS HISTORY INFORMATION | |
|---|---|---|---|---|---|---|---|---|
| | | | | | | | M0001 | M0002 |
| P0001 | V0001 | 1 | 60 | .. | 8.1 | .. | 0 | 0 |
| P0001 | V0002 | 1 | 60 | .. | 7.7 | .. | 500 | 0 |
| P0001 | V0003 | 1 | 60 | .. | 6.8 | .. | 1000 | 3 |
| ... | ... | ... | ... | ... | ... | ... | ... | ... |

202   1702   203   204   2306

BLOOD SUGAR CONTROL MEANS IMPLEMENTATION INFORMATION 2304

| M0001 | M0002 | ... |
|---|---|---|
| 500 | 0 | ... |
| 1000 | 3 | ... |
| 1000 | 3 | ... |
| ... | ... | ... |

BLOOD SUGAR CONTROL TARGET ACHIEVEMENT DETERMINATION INFORMATION 2301

| TARGET ID | TARGET VALUE | TARGET PERIOD | ACHIEVED VALUE | ACHIEVEMENT DETERMINATION |
|---|---|---|---|---|
| G0001 | 7.0 | 7.0 | 7.7 | 0 |
| G0001 | 7.0 | 7.0 | 6.8 | 1 |
| G0001 | 7.0 | 7.0 | 6.8 | 1 |
| ... | ... | ... | ... | ... |

| DRUG ID | CATEGORY | COMPOUND | ACTION MECHANISM | ... |
|---|---|---|---|---|
| M0001 | BIGUANIDES | METFORMIN | INSULIN RESISTANCE IMPROVEMENT | |
| M0002 | SULFONYLUREAS | GLYBURIDE | INSULIN SECRETION PROMOTION | |
| M0003 | SULFONYLUREAS | GLIPZIDE | INSULIN SECRETION PROMOTION | |
| M0004 | THIAZOLIDINEDIONES | PIOGLITAZONE | INSULIN RESISTANCE IMPROVEMENT | |
| M0005 | THIAZOLIDINEDIONES | ROSIGLITAZONE | INSULIN RESISTANCE IMPROVEMENT | |
| ... | ... | ... | ... | |

DRUG ACTION MECHANISM INFORMATION

Fig. 10

BLOOD SUGAR CONTROLLABILITY INFORMATION 2601

| BASIC INFORMATION | | BLOOD SUGAR CONTROLLABILITY | | | | BLOOD SUGAR CONTROLLABILITY ESTIMATION SCHEME |
|---|---|---|---|---|---|---|
| PATIENT ID | DIAGNOSIS-OR-TREATMENT ID | INSULIN RESISTANCE IMPROVEMENT | INSULIN SECRETION PROMOTION | SUGAR ABSORPTION REGULATION | SUGAR EXCRETION REGULATION | |
| P0001 | V0001 | 1 | 1 | 1 | 1 | M001 |
| P0001 | V0002 | 0.9 | 1 | 1 | 1 | M001 |
| P0001 | V0003 | 0.8 | 0.9 | 1 | 1 | M001 |
| ... | ... | ... | ... | ... | ... | ... |
| 202 | 1702 | 2602 | 2603 | 2604 | 2605 | 2606 |

*Fig. 12*

BLOOD SUGAR CONTROL MEANS SUGGESTION

[mg/dl]

○ BLOOD SUGAR CONTROLLABILITY ESTIMATION RESULT

| DATE | INSULIN RESISTANCE IMPROVEMENT | INSULIN SECRETION PROMOTION | SUGAR ABSORPTION REGULATION | SUGAR EXCRETION REGULATION |
|---|---|---|---|---|
| 20170920 | 0.6 | 0.8 | 1 | 1 |

○ SET BLOOD SUGAR CONTROL TARGET

- ITEM: HbA1c
- TARGET VALUE: 7.0
- TARGET ACHIEVEMENT PERIOD: 60 DAY  DAY

○ BLOOD SUGAR CONTROL MEANS SUGGESTION RESULT

○ TREATMENT MEANS SUGGESTION RESULT

| No. | TREATMENT MEANS | SUGGESTION SCORE Pp |
|---|---|---|
| 1 | ➤ SULFONYLUREA | 0.75 |
| 2 | DPP-4 | 0.60 |
| 3 | BIGUANIDE | 0.40 |

○ TREATMENT APPROPRIATENESS LEVEL Pa

- SGLT2 5%
- THIAZOLIDINE 10%
- DDP-4 INHIBITOR 15%
- SULFONYLUREA 20%
- BIGUANIDE 50%

○ TREATMENT GOAL ACHIEVEMENT LEVEL Ps

- BIGUANIDE 40%
- SULFONYLUREA 75%
- DDP-4 INHIBITOR 60%
- THIAZOLIDINE 30%
- SLGT2 80%

GOAL ACHIEVEMENT PROBABILITY 100%

○ SET SUGGESTION SCORE CALCULATION LOGIC

Ps → × → Pp
Pa → WEIGHT (0, 0.1, 1 APPROPRIATENESS LEVEL)

Fig. 16B

TREATMENT SELECTION SUPPORT SYSTEM AND METHOD

CLAIM OF PRIORITY

The present application claims priority from Japanese patent application JP 2017-223492 filed on Nov. 21, 2017, the content of which is hereby incorporated by reference into this application.

BACKGROUND OF THE INVENTION

This invention relates to a treatment selection support system.

Clinical guidelines are available as scientific evidence information for supporting patients and doctors in their decision making, and are widely used as determining factors for deciding appropriate treatment methods. However, the clinical guidelines are based on collective intelligence, and do not necessarily indicate an optimum treatment method for each individual patient. Therefore, in addition to the clinical guidelines, a doctor grasps the individual characteristics of each patient to decide an optimum treatment method for the patient. For example, in treatment with a drug, the kind of medicine and a prescribed amount thereof are decided in consideration of a large volume of information including an age, a weight, and other such basic characteristics of a patient, a case history, complicating diseases, and states of organ functions. In general, those pieces of information are stored in an electronic health record system or other such computer system, but are not organized in a form required for decision making, and it is difficult to comprehensively grasp all pieces of required information.

In addition, even when the organized information is available, a decision logic for decision making is complicated and also depends on the clinical experience of a doctor. This leads to a problem in that a workload is heavy for a doctor with insufficient experience, which makes it difficult for the doctor to make an accurate judgment. In view of this, in order to support doctors in selection of treatment, a technology for presenting secondary information generated from accumulated information on diagnosis and treatment performed in the past is expected.

As background arts in this technical field, the following related arts have been proposed. In WO 2012/80906 A1, there is described a method for medical judgement support. The method includes: receiving a current patient set of data relating to a current patient; comparing the current patient set of data to a plurality of previous patient sets of data, each of the previous patient sets of data corresponding to a previous patient; selecting one of the previous patient sets of data based on a level of similarity between the selected previous patient set of data and the current patient set of data; and providing the selected previous patient set of data to a user.

In JP 2014-71592 A, there is described a medication effect prediction system configured to display, when a medication effect information server 55 is searched based on a drug name and attribute information on a patient, average medication effect information indicating an average medication effect of the retrieved drug in chronological order on a monitor.

SUMMARY OF THE INVENTION

At the time of treatment, there are cases in which a treatment goal is individually set for each patient based on the state and treatment history of the patient. For example, when treatment means appropriate for achieving a treatment goal of controlling a specific examination value at a level equal to or smaller than a given value after a fixed period has elapsed after the treatment can be suggested based on past results, the suggestion is useful for a doctor's decision making. However, in the technology described in WO 2012/80906 A1, a technology for suggesting treatment means in consideration of a treatment goal is not disclosed, and appropriate treatment means cannot be suggested based on the treatment goal, which is different among patients. Therefore, this invention has an object to provide a system capable of suggesting treatment means that does not deviate from past diagnosis-and-treatment results and has a high treatment goal achievement level with respect to the treatment goal set for each patient.

There are also cases in which, when the treatment is prolonged in the treatment of diabetes, the same drug as used before decreases in effect, and becomes unable to achieve a control target relating to blood sugar. At this time, the doctor selects a drug predicted to be appropriate and highly effective from among drugs having a different action mechanism depending on a blood sugar control target for a patient, but decision criteria for the drug and its prescribed amount are unclear, and the decision has been made by trial and error. Therefore, when appropriate treatment means can be suggested for each patient based on past treatment results and the treatment goal, the suggestion is useful for a doctor's decision making. However, with the technology described in JP 2014-71592 A, it is difficult to suggest a drug depending on reduction in treatment effect that is based on a past treatment history and the blood sugar control target. Therefore, this invention has an object to provide a system capable of suggesting, in the treatment of diabetes, treatment means that does not deviate from the past diagnosis-and-treatment results and has the highest treatment goal achievement level with respect to the treatment goal set for each patient while taking into consideration the reduction in effect involved in continuous treatment.

The representative one of inventions disclosed in this application is outlined as follows. There is provided a treatment selection support system, which is configured to support selection of blood sugar control means for treatment of diabetes, the treatment selection support system including a computer including: an arithmetic unit configured to execute predetermined processing; a storage device coupled to the arithmetic unit; and a communication interface coupled to the arithmetic unit, the storage device being configured to store: action mechanism information in which the blood sugar control means is associated with an action mechanism category including at least sugar absorption regulation, sugar excretion regulation, insulin secretion promotion, and insulin resistance improvement; and formatted information including information on the treatment performed on a patient, the treatment selection support system comprising: a target achievement determination module configured to create target achievement determination information including an achievement level of a blood sugar control target for each blood sugar control means based on the formatted information; a blood sugar controllability estimation module configured to create blood sugar controllability information including a history of implementing the blood sugar control means for each action mechanism category; an achievement level prediction model creation module configured to create an achievement level prediction model for predicting the achievement level of the blood sugar control target based on the formatted information, the target achievement determination information, and the blood sugar controllability information; an appropriateness level calculation model creation module configured to create an appropriateness level calculation model for calculating an appropriateness level of the blood sugar control means based on the formatted information, the target achievement determination information, and the blood sugar controllability information; an achievement level prediction module configured to use the achievement level prediction model to predict the achievement level of the blood sugar control target for the patient for each blood sugar control means; an appropriateness level calculation module configured to use the appropriateness level calculation model to calculate the appropriateness level of the blood sugar control means for the patient; and a blood sugar control means suggestion module configured to provide information on the blood sugar control means appropriate for the patient based on the predicted achievement level and the calculated appropriateness level.

According to one aspect of this invention, it is possible to select treatment means that does not deviate from the past diagnosis-and-treatment results and has a high treatment goal achievement level with respect to the treatment goal set for each patient. In particular, in the treatment of diabetes, it is possible to select the treatment means that does not deviate from the past diagnosis-and-treatment results and has a high treatment goal achievement level with respect to the treatment goal set for each patient while taking into consideration the reduction in effect involved in continuous treatment for each drug action mechanism. Problems, configurations, and effects other than those described above are clarified by the following description of embodiments of this invention.

BRIEF DESCRIPTION OF THE DRAWINGS

The present invention can be appreciated by the description which follows in conjunction with the following figures, wherein:

FIG. 2 is a diagram for illustrating an example of the patient basic information according to the first embodiment;

FIG. 3 is a diagram for illustrating an example of the examination information according to the first embodiment;

FIG. 4 is a diagram for illustrating an example of the disease information according to the first embodiment;

FIG. 5 is a diagram for illustrating an example of the blood sugar control means implementation information according to the first embodiment;

FIG. 6 is a diagram for illustrating an example of the blood sugar control target information according to the first embodiment;

FIG. 7 is a flow chart of processing to be executed by the blood sugar control target achievement determination module according to the first embodiment;

FIG. 8 is a diagram for illustrating an example of the blood sugar control target achievement determination information according to the first embodiment;

FIG. 9 is a diagram for illustrating an example of the formatted information according to the first embodiment;

FIG. 10 is a diagram for illustrating an example of the drug action mechanism information according to the first embodiment;

FIG. 12 is a diagram for illustrating an example of blood sugar controllability information stored in the blood sugar controllability information storage module according to the first embodiment;

FIG. 16A and FIG. 16B are diagrams for illustrating a user interface screen according to the first embodiment.

DETAILED DESCRIPTION OF THE PREFERRED EMBODIMENTS

Figure 1:
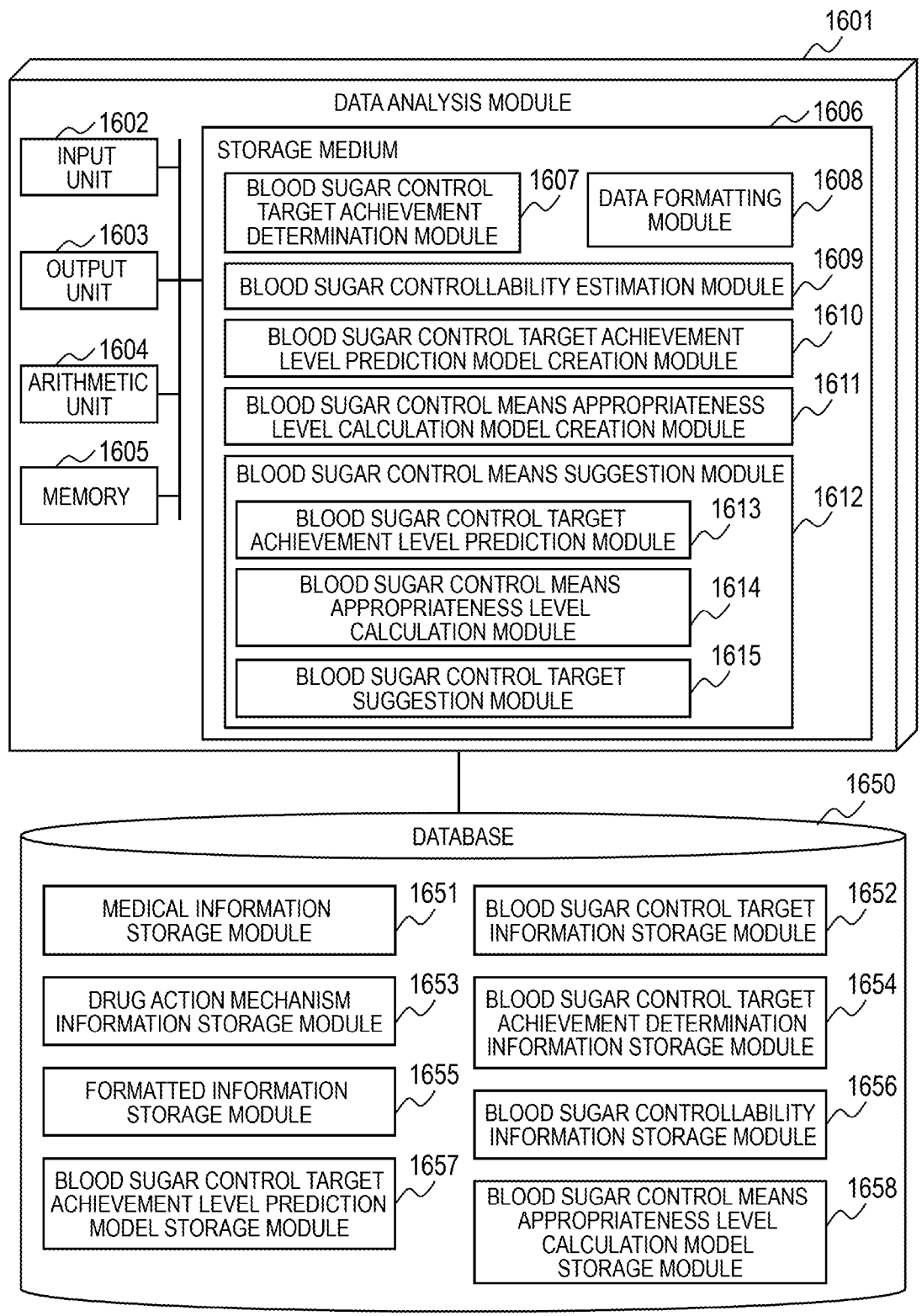
FIG. 1 a block diagram for illustrating a configuration of the treatment selection support system according to a first embodiment.

Now, embodiments for carrying out the invention are described with reference to the accompanying drawings.

First Embodiment

A first embodiment of this invention provides a treatment selection support system configured to achieve, in the treatment of diabetes, suggestion of treatment means that does not deviate from the past diagnosis-and-treatment results and has the highest treatment goal achievement level with respect to a treatment goal set for each patient while taking into consideration reduction in effect of a drug involved in continuous treatment. Specifically, in the treatment selection support system according to the first embodiment, blood sugar controllability for each patient is first estimated for each drug action mechanism based on a treatment history of diabetes and a history of a blood sugar level that were obtained in the past. Subsequently, a target achievement level of blood sugar control means for the treatment goal is predicted based on information on the patient and information on the blood sugar controllability. In addition, processing for evaluating an appropriateness level of the blood sugar control means is executed based on the information on the patient and the information on the blood sugar controllability. Lastly, appropriate blood sugar control means is suggested based on a score calculated through use of those two indices.

In the following, processing to be executed by the treatment selection support system according to the first embodiment, specifically, processing for calculating the treatment goal achievement level and the treatment means appropriateness level of each treatment means and suggesting the treatment means based on a combination of those two indices is described along with its effect. There is also described an effect of using the information on the blood sugar controllability, which is estimated for each patient, to calculate the treatment goal achievement level and the treatment means appropriateness level.

First, the treatment goal achievement level is described. The treatment goal achievement level is an index for predicting an achievement level of the treatment goal to be exhibited when the relevant treatment is carried out based on background information on a patient, for example, information including a gender, an age, an examination value, and a disease, and information on the past treatment history of the relevant patient. The treatment selection support system according to the first embodiment creates a model for predicting this index for each background of the patient and for each treatment means based on information on the treatment results for a previous patient, and predicts the treatment goal achievement level for each treatment when supporting the decision making. Through use of this index, it is possible to support the grasping of optimum treatment means for each individual patient in order to achieve the treatment goal set for each individual patient.

Next, the treatment means appropriateness level is described. The treatment means appropriateness level is an index indicating an appropriateness level for implementing the relevant treatment means based on the background information on the patient, for example, the information including the gender, the age, the examination value, and the disease, and the information on the past treatment history of the relevant patient. In this case, the appropriateness level is an index indicating, for example, to what degree the relevant treatment means was implemented on a similar patient in the past, and is an index calculated as, for example, the value of a probability that the relevant treatment means is assigned. The treatment selection support system according to the first embodiment creates, in advance, a calculation model that allows this index to be calculated for each patient and for each treatment means based on the information on the treatment results for the previous patient, and uses the relevant calculation model to calculate the treatment means appropriateness level for each treatment when supporting the decision making. Through use of this index, it is possible to support the grasping of treatment that matches patient characteristics, specifically, treatment means having treatment results close to results of treatment performed on a patient having a similar background of the patient among the past diagnosis-and-treatment results, for each individual patient.

Next, the effect of suggesting the treatment means based on the score calculated by combining the two indices of the treatment goal achievement level and the treatment means appropriateness level is described. In order to select a treatment appropriate for the treatment goal, it is desired to select a treatment expected to exhibit the highest achievement level of the treatment goal for the relevant patient. Meanwhile, the treatment means is not evenly selected for each patient, but is selected with a certain kind of bias depending on the background of the patient. Therefore, when the treatment means is proposed based only on the achievement level of the treatment goal without consideration of the bias, inappropriate treatment means may be proposed.

The description is given below by taking an example. For example, it is assumed that there are a drug A and a drug B, which act on the same examination value, and that the drug A has a small effect of suppressing the examination value, while the drug B has a larger effect of suppressing the examination value than that of the drug A. In this case, for example, it is predicted that the drug B exhibits a higher treatment goal achievement probability for the treatment goal of "controlling the examination value at a level equal to or smaller than a given value after prescription of a drug".

At this time, when there is past history information indicating that the effect of suppressing the examination value is large for the backgrounds of all patients, the drug B is suggested as treatment means appropriate for all the patients. Meanwhile, at an actual site of diagnosis or treatment, for example, in order to suppress excessive treatment using a drug, the drug B tends to be prescribed more frequently for patients having a higher examination value than the drug A, and it is assumed that the drug B has not been prescribed for the patients having a small examination value. In this case, a prescription pattern of prescribing the drug B for the patient having a small examination value becomes a treatment pattern that deviates from the actual diagnosis-and-treatment results. In view of this, the treatment selection support system according to the first embodiment uses the score obtained by combining the two indices of the treatment means appropriateness level and the treatment goal achievement level, to thereby be able to suggest a treatment that is highly likely to achieve the treatment goal without deviating from the treatment carried out in actuality.

Now, an additional effect of utilizing the treatment means appropriateness level is described. The treatment means appropriateness level is information on a tendency of treatment selection, which is determined based on the history information on the decision making at the actual site of diagnosis or treatment as to what kind of treatment means has been selected by the doctor for the patient having what kind of background. The information on the tendency of the treatment selection includes information on, for example, the decision of the prescribed amount adjusted based on the doctor's own experience in order to prevent overdose of the drug and the decision of the treatment means selected by the doctor based on his or her empirical judgment in order to avoid a side effect. Those pieces of information are information on collective intelligence of results of the doctor's actual decision making obtained at the clinical site, which is information obtained by accumulating results of a decision making process segmented from guidelines or other such medical consensus information. The treatment selection support system according to the first embodiment evaluates the treatment means together with the information on the treatment goal achievement level and the information on the treatment means appropriateness level, to thereby achieve the effect of selecting the treatment optimum for the treatment goal for the patient based on the decision making that does not contradict the results of judgment made by the doctor at the actual site of diagnosis or treatment.

Lastly, an outline of blood sugar controllability estimation used for calculating the treatment goal achievement level and the treatment means appropriateness level is described along with its effect. Diabetes is a chronic disease, and its treatment tends to be prolonged. At this time, as the treatment is prolonged, a constitution of the patient may be changed to decrease the effect with the same treatment as before. For example, it is known that, when such a kind of medicine as to promote the secretion of insulin is continuously prescribed, the function of pancreas is exhausted, and even when the same amount of drug is taken, the target of blood sugar control cannot sometimes be achieved. In this case, the doctor is required to select an operation of, for example, increasing the prescribed amount or switching to the drug having a different drug action mechanism, by trial and error while observing the patient's reaction to the drug.

The blood sugar controllability estimation is processing for alleviating a workload of the above-mentioned operation, in which past prescribed drug information recorded in the electronic system is classified by the drug action mechanism, and information obtained by aggregating the accumulated prescribed amount and the reduction in effect is estimated. Through estimation of the two levels of the treatment goal achievement level and the treatment means appropriateness level through use of the above-mentioned information, it is possible to suggest the blood sugar control means in consideration of the reduction in effect of the drug involved in the continuous treatment.

For example, in the prediction of the treatment goal achievement level, by considering long-term information on prescription patterns of drugs for each action mechanism in the past and information on a change in constitution of the patient, for example, information indicating which drug having which action mechanism is becoming ineffective, it is possible to predict a more accurate treatment goal achievement level for each individual patient. Meanwhile, the calculation of the treatment means appropriateness level has an effect that allows the doctor to use the past history information for each drug action mechanism to suggest the treatment means that does not deviate from a treatment pattern decided in consideration of the past information on a long-term treatment history.

Now, the treatment selection support system according to the first embodiment is described with reference to the accompanying drawings.

FIG. 1 is a block diagram for illustrating a configuration of the treatment selection support system according to the first embodiment. The treatment selection support system according to the first embodiment includes a data analysis module 1601 and a database 1650. The data analysis module 1601 includes an input unit 1602, an output unit 1603, an arithmetic unit 1604, a memory 1605, and a storage medium 1606.

The input unit 1602 is a mouse, a keyboard, or other such human interface, and receives input to the data analysis module 1601. The output unit 1603 is a display or a printer configured to output a processing result obtained by the treatment selection support system in a form visually recognizable by a user. The data analysis module 1601 may omit the input unit 1602 and the output unit 1603, and may receive the user's input through a terminal (not shown) coupled via a network to output the processing result.

The storage medium 1606 is a storage apparatus configured to store, for example, a program for achieving data analysis processing to be performed by the data analysis module 1601 and an execution result of the data analysis processing. The storage medium 1606 is formed of, for example, a large-volume nonvolatile storage apparatus (for example, magnetic disk drive or nonvolatile memory).

The memory 1605 includes a ROM being a nonvolatile storage element and a RAM being a volatile storage element. The ROM stores, for example, an unchangeable program (for example, BIOS). The RAM is a dynamic random access memory (DRAM) or other such high-speed volatile storage element, and temporarily stores the program stored in the storage medium 1606 and data to be used when the program is executed.

The arithmetic unit 1604 loads the program stored in the storage medium 1606 into the memory 1605, and executes the program, to thereby achieve a function of the data analysis module 1601. The arithmetic unit 1604 is, for example, a CPU or a GPU. Processing and arithmetic operations described later are executed by the arithmetic unit 1604. The processing performed by the arithmetic unit 1604 executing the program may be partially performed by hardware (for example, FPGA).

The database 1650 includes a medical information storage module 1651, a blood sugar control target information storage module 1652, a drug action mechanism information storage module 1653, a blood sugar control target achievement determination information storage module 1654, a formatted information storage module 1655, a blood sugar controllability information storage module 1656, a blood sugar control target achievement level prediction model storage module 1657, and a blood sugar control means appropriateness level calculation model storage module 1658.

The medical information storage module 1651 stores medical information. The medical information is information on a previous patient and a current patient, and includes patient basic information 201 including the gender and the age, which is shown in FIG. 2, examination information 1701 on an examination carried out in the past, which is shown in FIG. 3, disease information 1801 on diagnoses and treatments performed in the past, which is shown in FIG. 4, and blood sugar control means implementation information 1901 on blood sugar control means implemented in the past, which is shown in FIG. 5.

The blood sugar control target information storage module 1652 includes blood sugar control target information 2001 shown in FIG. 6, which is to be the target of the blood sugar control.

The drug action mechanism information storage module 1653 includes drug action mechanism information 2401 shown in FIG. 10, which is information on the action mechanism of a drug for each category.

The blood sugar control target achievement determination information storage module 1654 includes blood sugar control target achievement determination information 2201 shown in FIG. 8, which is created by a blood sugar control target achievement determination module 1607 based on the information included in the medical information storage module 1651 and the information included in the blood sugar control target information storage module 1652.

The formatted information storage module 1655 includes formatted information 2301 shown in FIG. 9, which is created by a data formatting module 1608 based on the information included in the medical information storage module 1651 and the information included in the blood sugar control target achievement determination information storage module 1654.

The blood sugar controllability information storage module 1656 includes information on the blood sugar controllability, an estimation scheme for the blood sugar controllability, and a model for estimating the blood sugar controllability, which are estimated by a blood sugar controllability estimation module 1609 based on the information included in the formatted information storage module 1655 and the information included in the drug action mechanism information storage module 1653.

The blood sugar control target achievement level prediction model storage module 1657 includes data on the model created by a blood sugar control target achievement level prediction model creation module 1610 based on the information included in the formatted information storage module 1655 and the information included in the blood sugar controllability information storage module 1656.

The blood sugar control means appropriateness level calculation model storage module 1658 includes data on the model created by a blood sugar control means appropriateness level calculation model creation module 1611 based on the information included in the formatted information storage module 1655 and the information included in the blood sugar controllability information storage module 1656.

A blood sugar control target achievement level prediction module 1613 predicts the blood sugar control target achievement level based on the model stored in the blood sugar control target achievement level prediction model storage module 1657.

A blood sugar control means appropriateness level calculation module 1614 predicts the blood sugar control target achievement level based on the model stored in the blood sugar control means appropriateness level calculation model storage module 1658.

A blood sugar control means suggestion module 1612 suggests the blood sugar control means based on the blood sugar control target achievement level predicted by the blood sugar control target achievement level prediction module 1613 and the appropriateness level calculated by the blood sugar control means appropriateness level calculation module 1614.

The program to be executed by the arithmetic unit 1604 is provided to the data analysis module 1601 via a removable medium (for example, CD-ROM or flash memory) or the network, and is stored in the nonvolatile storage medium 1606 being a non-transitory storage medium. Therefore, the data analysis module 1601 is preferred to include an interface for reading data from a removable medium.

The data analysis module 1601 and the database 1650 are each a computer system formed on physically one computer or on a plurality of computers formed logically or physically, and may operate on the same computer in separate threads, or may operate on a virtual machine built on a plurality of physical computer resources.

Now, different kinds of information and the respective processing modules 1607 to 1614 are described in detail. Of the components illustrated in FIG. 1, a blood sugar control target suggestion module 1615, which is not described in the first embodiment, is described in a second embodiment of this invention.

FIG. 2 is a diagram for illustrating an example of the patient basic information 201. The patient basic information 201 is information obtained by organizing basic information on patients for each patient. The patient basic information 201 includes, as its components, a patient ID 202, a gender 203, and an age 204. The patient ID 202 is an identifier for uniquely identifying a patient. The gender 203 and the age 204 are a gender and an age of the relevant patient, respectively.

FIG. 3 is a diagram for illustrating an example of the examination information 1701. The examination information 1701 is information obtained by organizing information on examinations carried out on the patients. The examination information 1701 includes, as its components, the patient ID 202, a diagnosis-or-treatment ID 1702, a date 1703, an item ID 1704, a value 1705, and a unit 1706. The patient ID 202 is the identifier for uniquely identifying the patient, which has the same definition as that of the patient ID 202 included in the patient basic information 201. The diagnosis-or-treatment ID 1702 is an identifier for uniquely identifying the relevant diagnosis or treatment carried out on the patient, for example, an identifier assigned in units of examinations and units of outpatient treatments. The date 1703 is a date on which the relevant examination was carried out, and may include information on a time at which the relevant diagnosis or treatment was carried out. The item ID 1704 is an identifier for uniquely identifying the kind of relevant examination. The value 1705 is information quantitatively or qualitatively indicating information on a result of the relevant examination. The unit 1706 is information indicating the unit of the value 1705. FIG. 3 is the diagram for illustrating the example including information on the value of HbA1c and the value of the patient's weight as the examination information.

FIG. 4 is a diagram for illustrating an example of the disease information 1801. The disease information 1801 is information obtained by organizing information on diseases of the patients. The disease information 1801 includes, as its components, the patient ID 202, the diagnosis-or-treatment ID 1702, the date 1703, and a disease ID 1802. The patient ID 202 is the identifier for uniquely identifying the patient, which has the same definition as that of the patient ID 202 included in the patient basic information 201. The diagnosis-or-treatment ID 1702 is an identifier for uniquely identifying the relevant diagnosis or treatment carried out on the patient, which has the same definition as that of the diagnosis-or-treatment ID 1702 included in the examination information 1701. The date 1703 is information on a date on which the information on the relevant disease was acquired, which has the same definition as that of the date 1703 included in the examination information 1701. The disease ID 1802 is information indicating a state of the disease of the patient, and includes, for example, code information indicating the kind of disease and code information indicating the relevant diagnosis or treatment.

FIG. 5 is a diagram for illustrating an example of the blood sugar control means implementation information 1901. The blood sugar control means implementation information 1901 is information obtained by organizing information on the blood sugar control means implemented on the patients. The blood sugar control means implementation information 1901 includes, as its components, the patient ID 202, the diagnosis-or-treatment ID 1702, the date 1703, a drug ID 1902, a prescribed amount 1903, and a unit 1904. The patient ID 202 is the identifier for uniquely identifying the patient, which has the same definition as that of the patient ID 202 included in the patient basic information 201. The diagnosis-or-treatment ID 1702 is an identifier for uniquely identifying the relevant diagnosis or treatment carried out on the patient, which has the same definition as that of the diagnosis-or-treatment ID 1702 included in the examination information 1701. The date 1703 is a date on which the relevant diagnosis or treatment was carried out, and the drug ID 1902 is an identifier for uniquely identifying the blood sugar control means implemented on the relevant patient. The prescribed amount 1903 is information on the prescribed amount of the relevant blood sugar control means (for example, drug). The unit 1904 is information indicating the unit of the prescribed amount 1903.

FIG. 6 is a diagram for illustrating an example of the blood sugar control target information 2001. The blood sugar control target information 2001 is information on a blood sugar control target. The blood sugar control target information 2001 includes, as its components, a target ID 2002, the item ID 1704, a target value 2003, a target period 2004, and a target period unit 2005. The target ID 2002 is an identifier for uniquely identifying the blood sugar control target. The item ID 1704 is an identifier for uniquely identifying the kind of an item being a subject of the target, for example, the kind of an examination value, which may have the same definition as that of the item ID 1704 included in the examination information 1701. The target value 2003 is a target value set for each piece of target information. The target period 2004 is a period to be required after the blood sugar control starts being carried out until the target achievement is determined. The target period unit 2005 is information indicating the unit of the target period 2004. The blood sugar control target information 2001 is created based on, for example, information input by the user through the input unit 1602.

Next, processing of the blood sugar control target achievement determination module 1607 is described. The blood sugar control target achievement determination module 1607 executes processing for determining whether or not the blood sugar control means implemented in the past has achieved the target of the blood sugar control.

FIG. 7 is a flow chart of processing to be executed by the blood sugar control target achievement determination module 1607.

First, in Step S2101, the examination information 1701 and the blood sugar control means implementation information 1901, which are stored in the medical information storage module 1651, are read and stored in the memory 1605.

In Step S2102, the blood sugar control target information 2001, which is stored in the blood sugar control target information storage module 1652, is read and stored in the memory 1605.

In Step S2103, the blood sugar control target achievement for each blood sugar control means is determined based on the examination information 1701, the blood sugar control means implementation information 1901, and the blood sugar control target information 2001, which are stored in the memory 1605, to create the blood sugar control target achievement determination information 2201 shown in FIG. 8. Details thereof are described below. First, the patient basic information 201, the examination information 1701, the blood sugar control means implementation information 1901, and the blood sugar control target information 2001 are formatted in association with one another for each patient ID and each diagnosis-or-treatment ID that are included in the blood sugar control means implementation information 1901 and for each target ID included in the blood sugar control target information 2001. Subsequently, for the respective sets of pieces of information associated with one another for each patient ID, each diagnosis-or-treatment ID, and each target ID, the value 1705 included in the examination information 1701 and acquired within the target period 2004 from the date 1703 included in the blood sugar control means implementation information 1901 is retrieved from the information on the item of the item ID 1704 included in the blood sugar control target information 2001, and the retrieved value is compared to the target value 2003, to thereby determine whether or not the target has been achieved.

The above-mentioned processing is specifically described below with reference to FIG. 3, FIG. 5, and FIG. 6 by taking data having the patient ID being P0001 and the diagnosis-or-treatment ID being V0001 as an example. This data indicates that, as shown in FIG. 5, a medicine having the drug ID being M0001 was prescribed on the date of Oct. 7, 2017. A description is given of an example of determining whether or not this patient has achieved a target having a target ID being G0001 included in the blood sugar control target information 2001 shown in FIG. 6. The target having the target ID being G0001 is defined so that the value of an examination item having the item ID being I0001 achieves the target value of 8.0 within 30 days defined by a target period and a target period unit. In the case of a patient having the patient ID being P0001, a treatment having the diagnosis-or-treatment ID being V0001 was carried out on Oct. 7, 2017, and hence examination information having the item ID being I0001 is retrieved from among pieces of examination information having a date within 30 days from the above-mentioned date to determine whether or not the target has been achieved. In the case of this example, the examination information 1701 includes data having the value being 7.7 on Nov. 6, 2017, that is, includes examination data having a value equal to or smaller than the target value, and hence it is determined that the target has been achieved.

Some examples of a target achievement determination method are described. In the first embodiment, any method may be employed depending on the characteristics of the disease, the treatment, and the examination. A first method is a method of determining that the target has been achieved when the value was achieved at least once during the target period. A second method is a method of determining that the target has been achieved when the target was achieved at least a specific number of times during the target period. A third method is a method of determining that the target has been achieved when there is no examination information in which the target value was never achieved during the target period.

FIG. 8 is a diagram for illustrating an example of the blood sugar control target achievement determination information 2201. The blood sugar control target achievement determination information 2201 includes the patient ID 202, the diagnosis-or-treatment ID 1702, the target ID 2002, an achieved value 2202, and an achievement determination 2203. The patient ID 202, the diagnosis-or-treatment ID 1702, and the target ID 2002 include the same kinds of information as those of information included in FIG. 2, FIG. 3, and FIG. 6, respectively. The patient ID 202 is the identifier for uniquely identifying the patient, which has the same definition as that of the patient ID 202 included in the patient basic information 201. The diagnosis-or-treatment ID 1702 is the identifier for uniquely identifying the relevant diagnosis or treatment carried out on the patient, which has the same definition as that of the diagnosis-or-treatment ID 1702 included in the examination information 1701. The target ID 2002 is the identifier for uniquely identifying the treatment goal, which has the same definition as that of the target ID 2002 included in the blood sugar control target information 2001. The achieved value 2202 is a value (for example, value 1705 of an examination result) obtained when the target was achieved. The achievement determination 2203 is information indicating whether or not the target has been achieved, and can be expressed by, for example, binary information including "TRUE" or "FALSE", symbolic information including "T" or "F", or numerical information including "1" or "0". The achievement determination 2203 may also be information expressed by a continuous value. For example, a difference between a value set as the target value and a value that has achieved (or has not achieved) the target value may be calculated, and the value of the calculated difference may be recorded in the achievement determination 2203.

When there is no examination information having the relevant item ID during the target period, the data on the blood sugar control target achievement determination information 2201 may not be created, or data in which information indicating that the data has not been acquired is recorded in the achievement determination 2203 may be created.

In Step S2104, the blood sugar control target achievement determination information 2201 created in Step S2103 is output and stored in the blood sugar control target achievement determination information storage module 1654.

Next, processing to be executed by the data formatting module 1608 is described. The data formatting module 1608 formats patient basic information, examination information, disease information, and treatment information that are stored in the medical information storage module 1651 and the blood sugar control target achievement determination information 2201 stored in the blood sugar control target achievement determination information storage module 1654 to create one piece of formatted information. The formatted information integrally includes an implementation situation of the blood sugar control means, information on a patient for which the blood sugar control means was implemented, and a target achievement result of the blood sugar control means, and is used for different kinds of model creation processing described later. Details of the formatted information are described below.

FIG. 9 is a diagram for illustrating an example of the formatted information 2301. The formatted information 2301 is information obtained by organizing, for each patient ID, each target ID, and each diagnosis-or-treatment ID, the basic information on the patient, the examination information, the disease information, implementation information on the blood sugar control means implemented for the relevant diagnosis-or-treatment ID, the history information on the blood sugar control means implemented in the past, and information on the presence or absence of blood sugar control target achievement.

The formatted information 2301 includes medical information 2302, blood sugar control means history information 2303, blood sugar control means implementation information 2304, and blood sugar control target achievement determination information 2305. The medical information 2302 includes the basic information and the state of health of the relevant patient exhibited when the diagnosis or treatment was carried out, and specifically includes the patient ID 202, the diagnosis-or-treatment ID 1702, the gender 203, the age 204, information on the examination value (for example, HbA1c value 2306), information on the disease, and information on the relevant diagnosis or treatment.

The blood sugar control means history information 2303 is information obtained by organizing information on the blood sugar control means implemented before a day on which the relevant diagnosis or treatment was carried out, and includes, for example, information obtained by aggregating information on a drug continuously prescribed until a day on which the relevant diagnosis or treatment was carried out and information on drugs prescribed during the past 30 days. This aggregation may be, for example, binary information indicating the presence or absence of prescription for each drug, or the prescribed amount of each drug may be directly used. As a ratio with respect to a prescribed upper limit amount set for each drug, a value equal to or larger than 0 and equal to or smaller than 1 may be used as an index indicating the prescribed amount.

The blood sugar control means implementation information 2304 is information obtained by organizing information on the blood sugar control means implemented in the relevant diagnosis or treatment. For example, the blood sugar control means implementation information 2304 is information obtained by aggregating the information on the drug prescribed on the day on which the relevant diagnosis or treatment was carried out. This aggregation may be, for example, the binary information indicating the presence or absence of the prescription for each drug, or the prescribed amount of each drug may be directly used. As the ratio with respect to the prescribed upper limit amount set for each drug, the value equal to or larger than 0 and equal to or smaller than 1 may be used as the index indicating the prescribed amount. The blood sugar control target achievement determination information 2305 is the information indicating whether or not the blood sugar control target has been achieved through implementation of the relevant blood sugar control means. Specifically, data associated with the relevant blood sugar control means implementation information 2304 in the blood sugar control target achievement determination information 2201 is stored.

When the formatted information 2301 is to be created, all category variables may be converted into numerical variables. For example, the information on the gender 203 may be converted into a numerical value of 1 indicating male and a numerical value of 2 indicating female. Also in regard to the blood sugar control means history information 2303 and the blood sugar control means implementation information 2304, when the prescribed amount has different units for each drug, the information may be normalized or standardized as the value of the ratio with respect to the prescribed upper limit amount. The information on the achievement determination 2203 may be converted into a numerical value of 1 indicating an achieved state and a numerical value of 0 indicating an unachieved state. Such conversion produces an effect that an applicable range of an arithmetic operation is enlarged in numerical calculation processing for different kinds of model creation processing described later and blood sugar controllability estimation processing. The created formatted information 2301 is stored in the formatted information storage module 1655.

In the first embodiment, as shown in FIG. 9, the formatted information 2301 having such a format that the information on the treatment means implemented for the patient in the past is organized for each patient, for each treatment means, and for each timing at which the treatment means was assigned, but any other format that includes the information on the treatment means implemented for the patient in the past may be employed.

Next, the blood sugar controllability estimation module 1609 is described. The blood sugar controllability estimation module 1609 estimates the blood sugar controllability for each patient and for each timing of diagnosis or treatment based on the formatted information 2301 stored in the formatted information storage module 1655 and drug action mechanism information stored in the drug action mechanism information storage module 1653, and stores the estimated blood sugar controllability in the blood sugar controllability information storage module 1656. The blood sugar controllability is an index indicating effectiveness with respect to the patient for each action mechanism of the blood sugar control means, and is estimated based on a relationship between the history of treatments carried out on the patient in the past and information indicating whether or not the treatment goal was successfully achieved in the relevant history of treatments carried out.

An object of estimating the blood sugar controllability in this treatment selection support system is described. As the treatment of diabetes is prolonged, the effect may decrease with the same drug as before, and the object of lowering blood sugar may fail to be achieved. For example, it is known that, as a treatment with medication using such a kind of drug as to promote the secretion of insulin is prolonged, the insulin secretion capability of pancreas may be weakened to inhibit the effect from occurring even with the prescription of a medicine having the same action mechanism. In this manner, in the treatment of diabetes, it is important to determine the medication by chronologically considering the action mechanism of the drug prescribed in the past, a prescribed period thereof, and the continuous effectiveness of the effect of the relevant drug. In view of this, the blood sugar controllability is estimated from the pattern of medication in the past and its effect, and an appropriate drug is suggested based on this information, to thereby achieve more accurate suggestion of the treatment with medication.

First, with reference to FIG. 10, a description is given of the drug action mechanism information used for the blood sugar controllability estimation. FIG. 10 is a diagram for illustrating an example of the drug action mechanism information 2401. The drug action mechanism information 2401 is information including information on the drug action mechanism for each blood sugar control means. The drug action mechanism information 2401 includes, as its components, the drug ID 1902, a category 2402, a compound 2403, and an action mechanism 2404. The drug ID 1902 has the same definition as that of the drug ID 1902 included in the blood sugar control means implementation information 1901. The category 2402 is information indicating the category of a drug being the blood sugar control means. The compound 2403 is information indicating a compound included in the drug. The action mechanism 2404 is the information indicating the category of the action mechanism of the drug, and includes, for example, insulin resistance improvement, insulin secretion promotion, sugar excretion regulation, sugar absorption regulation, and other such category information.

Figure 11:
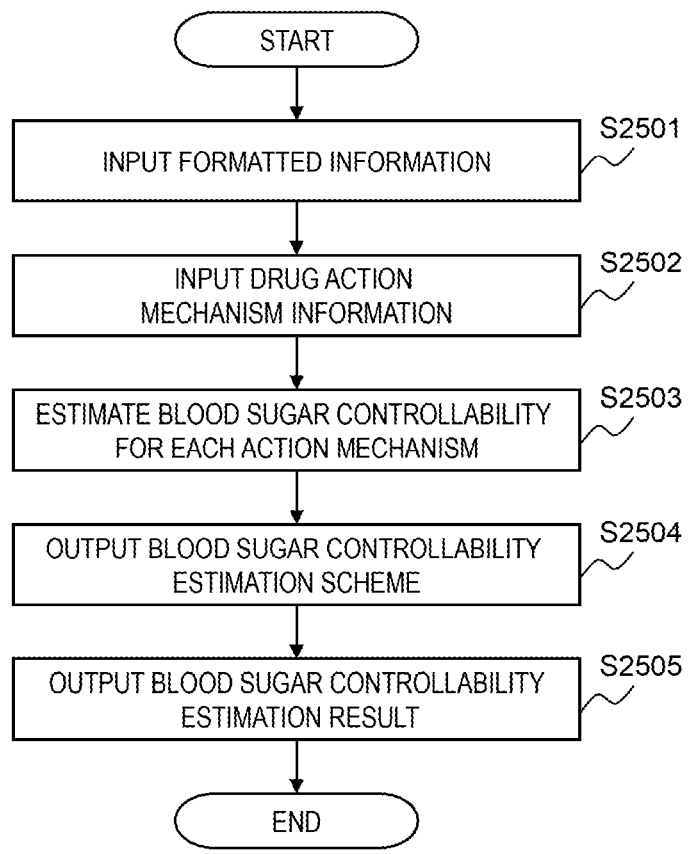
FIG. 11 is a flow chart of processing to be executed by the blood sugar controllability estimation module according to the first embodiment.

Next, with reference to FIG. 11, a description is given of processing to be executed by the blood sugar controllability estimation processing. FIG. 11 is a flow chart of processing to be executed by the blood sugar controllability estimation module 1609. Now, respective processing steps thereof are described.

In Step S2501, the formatted information 2301 stored in the formatted information storage module 1655 is read.

In Step S2502, the drug action mechanism information 2401 stored in the drug action mechanism information storage module 1653 is read.

In Step S2503, the blood sugar controllability for each patient and each diagnosis-or-treatment ID is estimated for each drug action mechanism based on the formatted information 2301 and the drug action mechanism information 2401.

Some examples of a method of estimating the blood sugar controllability are described. In the first embodiment, any method may be employed. A first method is a method involving summarizing, for each relevant patient and for each diagnosis-or-treatment ID, the history information on the blood sugar control means implemented before the day associated with the relevant diagnosis-or-treatment ID for each drug action mechanism based on the drug action mechanism information 2401, and setting the information obtained by aggregating the prescription history information for each drug action mechanism as the blood sugar controllability. For example, the accumulated prescribed amount of the drug prescribed during the past one year from the date associated with the diagnosis-or-treatment ID is summarized for each drug action mechanism. As the summarized information, for example, the summarized amount may be used as it is, or may be converted into such a numerical value index as to become larger as the accumulated prescribed amount becomes smaller and as to become smaller as the accumulated prescribed amount becomes larger, the converted numerical value index may be used as the blood sugar controllability. The prescribed period may be used in place of the prescribed amount. With the first method, it is possible to estimate the blood sugar controllability for each drug action mechanism for the patient from the information on the accumulated prescribed amount or the prescribed period for each drug action mechanism for the patient in the past.

A second method is a method involving summarizing, for each relevant patient and for each diagnosis-or-treatment ID, the history information on the blood sugar control means implemented before the day associated with the relevant diagnosis-or-treatment ID for each drug action mechanism based on the drug action mechanism information 2401, and estimating the blood sugar controllability based on a result of analyzing relevance between the information obtained by aggregating the prescription history information for each drug action mechanism and the information on a change of the examination value focused on as a subject of the treatment goal. For example, a model (for example, regression model) indicating a relation among the continuous prescribed period in the past for each drug action mechanism, the medical information 2302 on the patient, and a change amount of the examination value is created. After this regression model is created through use of all pieces of data included in the formatted information 2301, information on an expected value of prediction of the change amount of each examination value predicted for each patient ID and each diagnosis-or-treatment ID is used as the information on the blood sugar controllability. With the second method, it is possible to calculate, for example, numerical value information indicating a difference in influence exerted on the examination value between a case of newly prescribing a drug having a given drug action mechanism and a case of continuously prescribing the drug.

A third method is a method involving creating a model indicating a relationship between chronological prescription results for each drug action mechanism for the patient and chronological treatment effects, and extracting the information on the blood sugar controllability from the created model. First, information is created from among the respective records included in the formatted information by aggregating the blood sugar control means history information 2303 and the blood sugar control means implementation information 2304 for each drug action mechanism based on the drug action mechanism information 2401. As an aggregation method, for example, the prescribed amount of each drug may be expressed by the ratio with respect to the maximum prescribed amount, and the values may be summed up, to thereby perform the aggregation. Next, the blood sugar control means history information 2303 and the blood sugar control means implementation information 2304, which are aggregated for each drug action mechanism, and the medical information 2302 on the patient are expressed by a vector indicating the state of the patient exhibited at a given time point. A model for predicting a chronological transition of the vectors for each patient is created based on information on a vector array obtained by arranging the vectors in chronological order in units of patients, and the information on the blood sugar controllability is extracted from the created model. As a modeling method, a model having a time-series internal state is created in accordance with the chronological transition. For example, it is possible to use a state space model that takes a time series into consideration or a deep learning model that takes a time series into consideration, for example, long short-term memory (LSTM) or other such known method. Then, the information on the blood sugar controllability in each of chronological steps is estimated from the created model. For example, in the case of using the LSTM, all pieces of information on the patient are first used to create a model for predicting the vector at the subsequent chronological step. Subsequently, at each chronological step for each patient, all pieces of chronological information in the past are input to carry out the prediction, and the information on an internal state vector acquired at that time is handled as the information on the blood sugar controllability. This internal state is estimated for each patient, for each diagnosis-or-treatment ID, and for each drug action mechanism, and the vector indicating the internal state is estimated as the blood sugar controllability.

In Step S2504, a blood sugar controllability estimation scheme employed in Step 2503 is stored in the blood sugar controllability information storage module 1656. For example, processing and arithmetic operation methods for an estimation formula, a logic, a model, and other such information used for the estimation are stored in a form usable by the arithmetic unit 1604.

In Step S2505, the information on the blood sugar controllability estimated in Step S2503 is stored in the blood sugar controllability information storage module 1656.

FIG. 12 is a diagram for illustrating an example of blood sugar controllability information 2601 stored in the blood sugar controllability information storage module 1656. In addition to the patient ID 202 and the diagnosis-or-treatment ID 1702, the blood sugar controllability information 2601 includes, for example, insulin resistance improvement 2602, insulin secretion promotion 2603, sugar absorption regulation 2604, sugar excretion regulation 2605, and other such information as the blood sugar controllability. In addition, the blood sugar controllability information 2601 includes a blood sugar controllability estimation scheme 2606.

Each of the pieces of information 2602 to 2605 included in the blood sugar controllability is an index indicating a period during which the drug having each action mechanism has already been prescribed for the patient and the effect of the drug having the relevant action mechanism, and is expressed by, for example, a value equal to or larger than 0 and equal to or smaller than 1 in this example. For example, the index value of 1 indicates that the drug has never been prescribed. Meanwhile, the index value of 0 indicates that it is difficult to change blood sugar as a result that the same drug has been continuously prescribed.

The blood sugar controllability estimation scheme 2606 stores the blood sugar controllability estimation scheme employed in Step 2503, for example, the estimation formula, logic, model, or other such information used for the estimation, in a form usable by the arithmetic unit 1604 (for example, file name or information for activating the relevant scheme).

Next, the blood sugar control target achievement level prediction model creation module 1610 is described. The blood sugar control target achievement level prediction model creation module 1610 creates a blood sugar control target achievement level prediction model for predicting the target achievement level of each blood sugar control means for each patient and each blood sugar control means.

Figure 13:
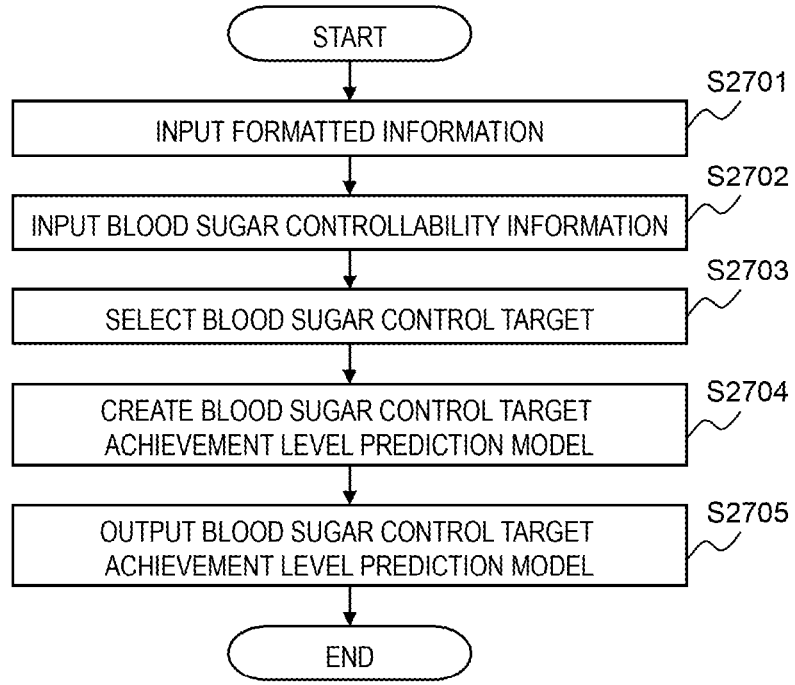
FIG. 13 is a flow chart of processing to be executed by the blood sugar control target achievement level prediction model creation module according to the first embodiment.

FIG. 13 is a flow chart of processing to be executed by the blood sugar control target achievement level prediction model creation module 1610. Now, respective processing steps thereof are described.

In Step S2701, the formatted information 2301 stored in the formatted information storage module 1655 is read.

In Step S2702, the blood sugar controllability information 2601 stored in the blood sugar controllability information storage module 1656 is read.

In Step S2703, pieces of information matching a specific target ID, which are to be used for creating the blood sugar control target achievement level prediction model, among the pieces of information stored in the formatted information 2301 are extracted from the formatted information 2301. For example, when the blood sugar control target achievement level prediction model relating to the target ID of G0001 is to be created, pieces of information having the target ID matching G0001 are extracted from the formatted information 2301. In addition, the pieces of information 2602 to 2605 in the blood sugar controllability having the patient ID 202 and the diagnosis-or-treatment ID 1702 matching those of the extracted pieces of information in the formatted information 2301 associated with the target ID are extracted from the blood sugar controllability information 2601.

In Step S2704, the blood sugar control target achievement level prediction model is created based on the formatted information 2301 and the blood sugar controllability information 2601 that are extracted based on the blood sugar control target determined in Step S2703. The blood sugar control target achievement level prediction model is a model for predicting the information on the achievement determination 2203 of the target included in the formatted information 2301 for each patient and each blood sugar control means based on the information on the patient and the information on the blood sugar controllability.

Some examples of the blood sugar control target achievement level prediction model are described. In the first embodiment, any method may be employed to create the blood sugar control target achievement level prediction model. A first model is a model for predicting a probability of whether or not the blood sugar control target is to be achieved. A second model is a model for predicting the value of a difference between an achieved value and the target value of the blood sugar control target. A combination of all or some of pieces of information included in the medical information 2302, the blood sugar control means history information 2303, the blood sugar control means implementation information 2304, and the blood sugar controllability information 2601 is used as variables to be input to the blood sugar control target achievement level prediction model. For example, a logistic regression, a Bayesian network using machine learning, multilayer perceptron, a boosting tree, and other such various kinds of statistical models can be used as the model for predicting the probability of whether or not the blood sugar control target is to be achieved.

In Step S2705, the blood sugar control target achievement level prediction model created in Step 2703 is stored in the blood sugar control target achievement level prediction model storage module 1657 together with the target ID of the corresponding blood sugar control target and the information on the blood sugar controllability estimation scheme used for estimating the blood sugar controllability read in Step S2702.

Next, the blood sugar control means appropriateness level calculation model creation module 1611 is described. The blood sugar control means appropriateness level calculation model creation module 1611 creates a blood sugar control means appropriateness level calculation model for predicting the appropriateness level of each blood sugar control means for each patient and each diagnosis or treatment.

Figure 14:
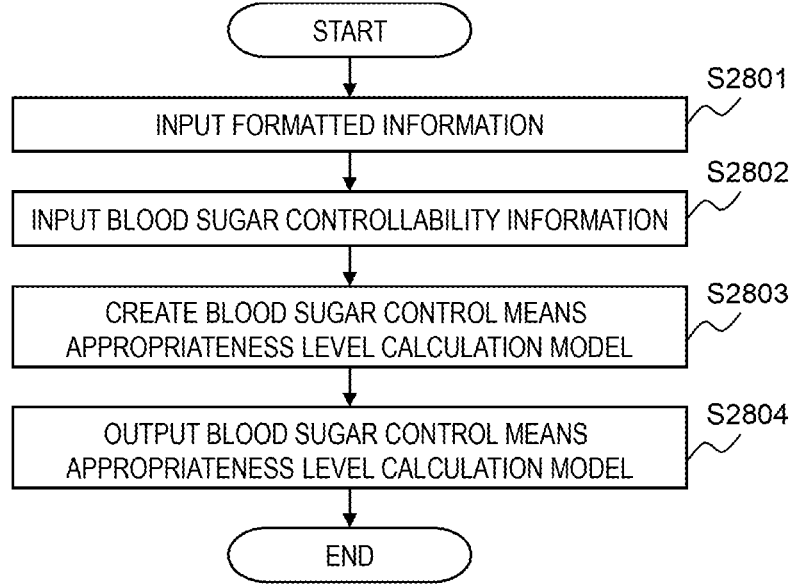
FIG. 14 is a flow chart of processing to be executed by the blood sugar control means appropriateness level calculation model creation module according to the first embodiment.

FIG. 14 is a flow chart of processing to be executed by the blood sugar control means appropriateness level calculation model creation module 1611. Now, respective processing steps thereof are described.

In Step S2801, the formatted information 2301 stored in the formatted information storage module 1655 is read.

In Step S2802, the blood sugar controllability information 2601 stored in the blood sugar controllability information storage module 1656 is read.

In Step S2803, the blood sugar control means appropriateness level calculation model is created based on the formatted information 2301 and the blood sugar controllability information 2601. The blood sugar control means appropriateness level calculation model is a model for predicting the appropriateness level of the blood sugar control means included in the formatted information 2301 for each patient and the blood sugar control means. Some examples of the blood sugar control means appropriateness level calculation model are described. In the first embodiment, any method may be employed to create the blood sugar control means appropriateness level calculation model depending on the characteristics of the blood sugar control means. A first model is a model for predicting a probability that the relevant blood sugar control means is assigned to each patient based on the past information. A second model is a model for predicting the number of patients suffering from a similar case of the disease in the past in which the relevant blood sugar control means was assigned to each patient. A combination of all or some of pieces of information included in the medical information 2302, the blood sugar control means history information 2303, the blood sugar control means implementation information 2304, and the blood sugar controllability information 2601 is used as variables to be input to the blood sugar control means appropriateness level calculation model. For example, a logistic regression, a Bayesian network using machine learning, multilayer perceptron, a boosting tree, and other such various kinds of methods for statistical model can be used as a mode of the prediction model.

In Step S2804, the blood sugar control means appropriateness level calculation model created in Step 2803 is stored in the blood sugar control means appropriateness level calculation model storage module 1658 together with the information on the blood sugar controllability estimation scheme used for estimating the blood sugar controllability read in Step S2802.

Next, the blood sugar control means suggestion module 1612 is described. The blood sugar control means suggestion module 1612 suggests appropriate blood sugar control means for each patient. Specifically, the blood sugar control means suggestion module 1612 includes the blood sugar control target achievement level prediction module 1613 and the blood sugar control means appropriateness level calculation module 1614. For each blood sugar control means, the blood sugar control means suggestion module 1612 evaluates the blood sugar control target achievement level, and the blood sugar control target achievement level prediction module 1613 evaluates the blood sugar control means appropriateness level. After that, the two indices of the blood sugar control target achievement level and the blood sugar control means appropriateness level are combined with each other to calculate a score for evaluating the blood sugar control means, and appropriate blood sugar control means is suggested for the patient based on the calculated score.

Figure 15:
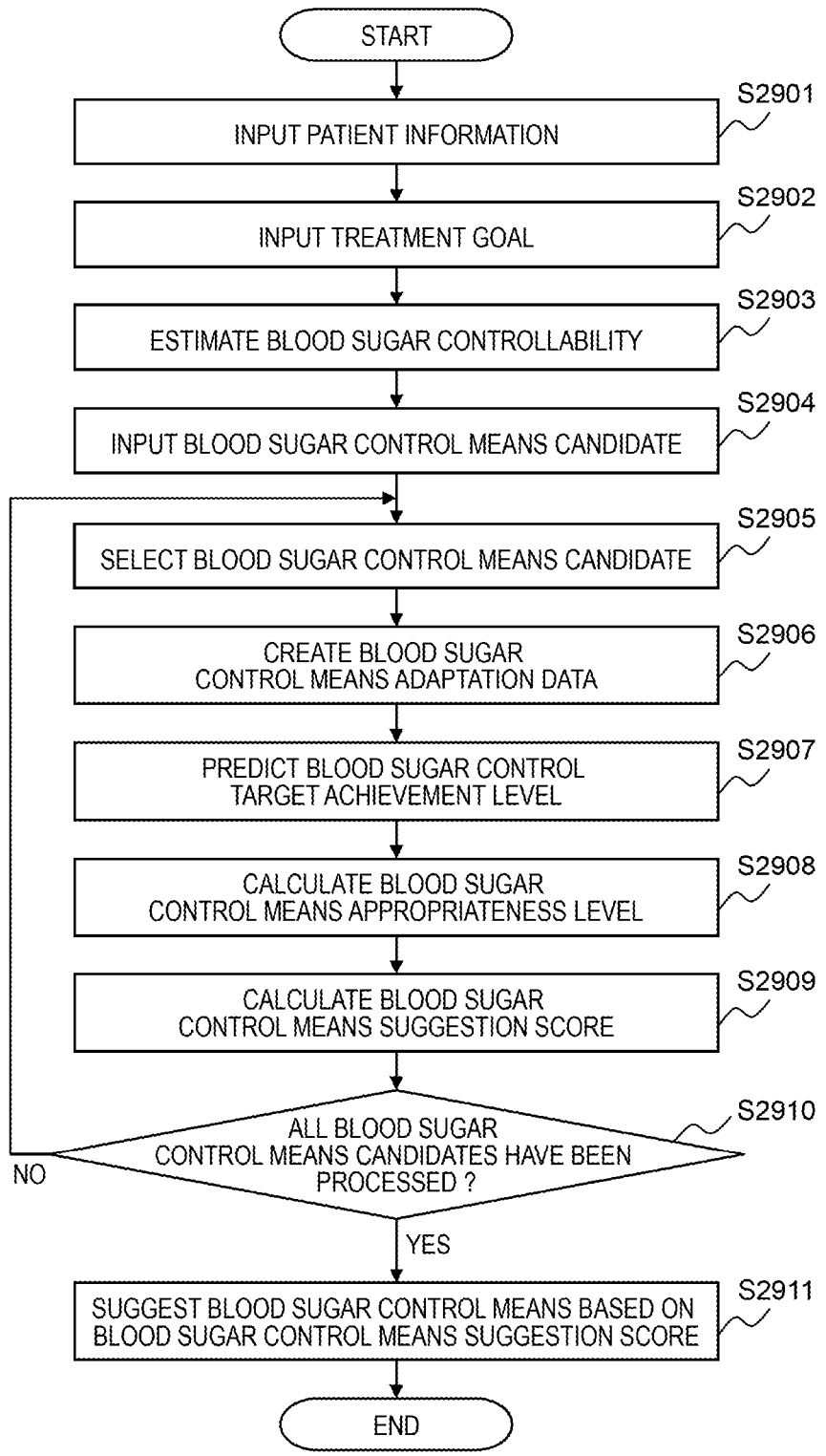
FIG. 15 is a flow chart of processing to be executed by the blood sugar control means suggestion module according to the first embodiment.

FIG. 15 is a flow chart of processing to be executed by the blood sugar control means suggestion module 1612. Now, respective processing steps thereof are described.

In Step S2901, the patient basic information 201 on the patient for which the blood sugar control means is to be suggested is input to the blood sugar control means suggestion module 1612. The information to be input includes the examination information 1701 including the age and the gender, the disease information 1801 obtained in the past, and the blood sugar control means implementation information 1901. At this time, the input information is formatted in the same format as that of the formatted information 2301 stored in the formatted information storage module 1655, and is stored in the memory 1605.

In Step S2902, the target of the blood sugar control is input to the blood sugar control means suggestion module 1612. For example, as the target of the blood sugar control, appropriate information on the blood sugar control target may be selected from the blood sugar control target information 2001 stored in the blood sugar control target information storage module 1652.

In Step S2903, the blood sugar controllability for the subject patient is estimated based on the formatted information formatted in Step S2901. Specifically, the blood sugar controllability estimation scheme to be applied to the subject patient is selected from among the blood sugar controllability estimation schemes 2606 in the blood sugar controllability information 2601 stored in the blood sugar controllability information storage module 1656, and the blood sugar controllability is estimated by the same method as that used for estimating relevant blood sugar controllability information. As the estimation scheme for the blood sugar controllability, a predetermined estimation scheme may be used, or a method appropriate for each individual patient may be designated by the user.

In Step S2904, a candidate for the blood sugar control means is input to the blood sugar control means suggestion module 1612. For example, the blood sugar control means may be supplied as a set of some specific drug names, or may be supplied as a granularity of a category for organizing similar drugs.

In Step S2905, the blood sugar control means suggestion module 1612 selects one blood sugar control means for carrying out the prediction from among candidates for the blood sugar control means.

In Step S2906, the blood sugar control means suggestion module 1612 creates virtual means adaptation data to be obtained when the blood sugar control means is applied to the patient. Specifically, the information on the predicted blood sugar control means is virtually stored in the blood sugar control means implementation information 2304 in the formatted information 2301, and a record indicating a scenario to be used when the blood sugar control means is implemented is created.

In Step S2907, the blood sugar control target achievement level prediction module 1613 predicts the target achievement level to be exhibited when the blood sugar control means is applied based on the virtual means adaptation data created in Step S2906. Specifically, the blood sugar control target achievement level prediction module 1613 predicts the target achievement level of the relevant blood sugar control means through use of the blood sugar control target achievement level prediction model corresponding to the blood sugar control target selected in Step S2902 among blood sugar control target achievement level prediction models stored in the blood sugar control target achievement level prediction model storage module 1657.

In Step S2908, the blood sugar control means appropriateness level calculation module 1614 uses the blood sugar control means appropriateness level calculation model stored in the blood sugar control means appropriateness level calculation model storage module 1658 to calculate the appropriateness level of the blood sugar control means based on the virtual means adaptation data created in Step S2906.

In Step S2909, the blood sugar control means suggestion module 1612 calculates a blood sugar control means suggestion score of the blood sugar control means to be predicted. The blood sugar control means suggestion score is calculated based on the two indices of the target achievement level predicted in Step S2907 and the appropriateness level calculated in Step S2908.

Some examples of a method of calculating the blood sugar control means suggestion score are described. In the first embodiment, any method may be employed depending on the characteristics of the target. A first method is a method involving setting a result of one of the four fundamental arithmetic operations between the goal achievement probability and the appropriateness level as the blood sugar control means suggestion score. For example, a product of the two indices can be set as a new score. A second method is a method involving defining an activation function based on the appropriateness level, and calculating the blood sugar control means suggestion score by multiplying the value of the defined activation function by the goal achievement probability. For example, such an activation function as to return 0 when the appropriateness level is equal to or smaller than a threshold value and return the value of the appropriateness level itself when the appropriateness level is larger than the threshold value is defined. When the appropriateness level is equal to or smaller than a given threshold value, 0 is set as the blood sugar control means suggestion score, and otherwise the product of the two indices is set as the blood sugar control means suggestion score.

In Step S2910, the blood sugar control means suggestion module 1612 determines whether or not the blood sugar control means suggestion score has been calculated for all the candidates for the blood sugar control means. When the calculation of the blood sugar control means suggestion score has been finished for all the candidates for the blood sugar control means, the procedure advances to Step S2911. Meanwhile, when the calculation of the blood sugar control means suggestion score has not been finished for a part of the candidates for the blood sugar control means, the procedure advances to Step S2905.

In Step S2911, the blood sugar control means suggestion module 1612 suggests appropriate blood sugar control means based on the score calculated for each blood sugar control means.

Some examples of a method of suggesting the treatment means are described. In the first embodiment, any method may be employed. A first method is a method involving suggesting the blood sugar control means having the maximum blood sugar control means suggestion score. A second method is a method involving suggesting at least one blood sugar control means having the blood sugar control means suggestion score equal to or larger than a threshold value. For example, the suggested blood sugar control means is presented to the user by the output unit 1603.

Figure 16A:
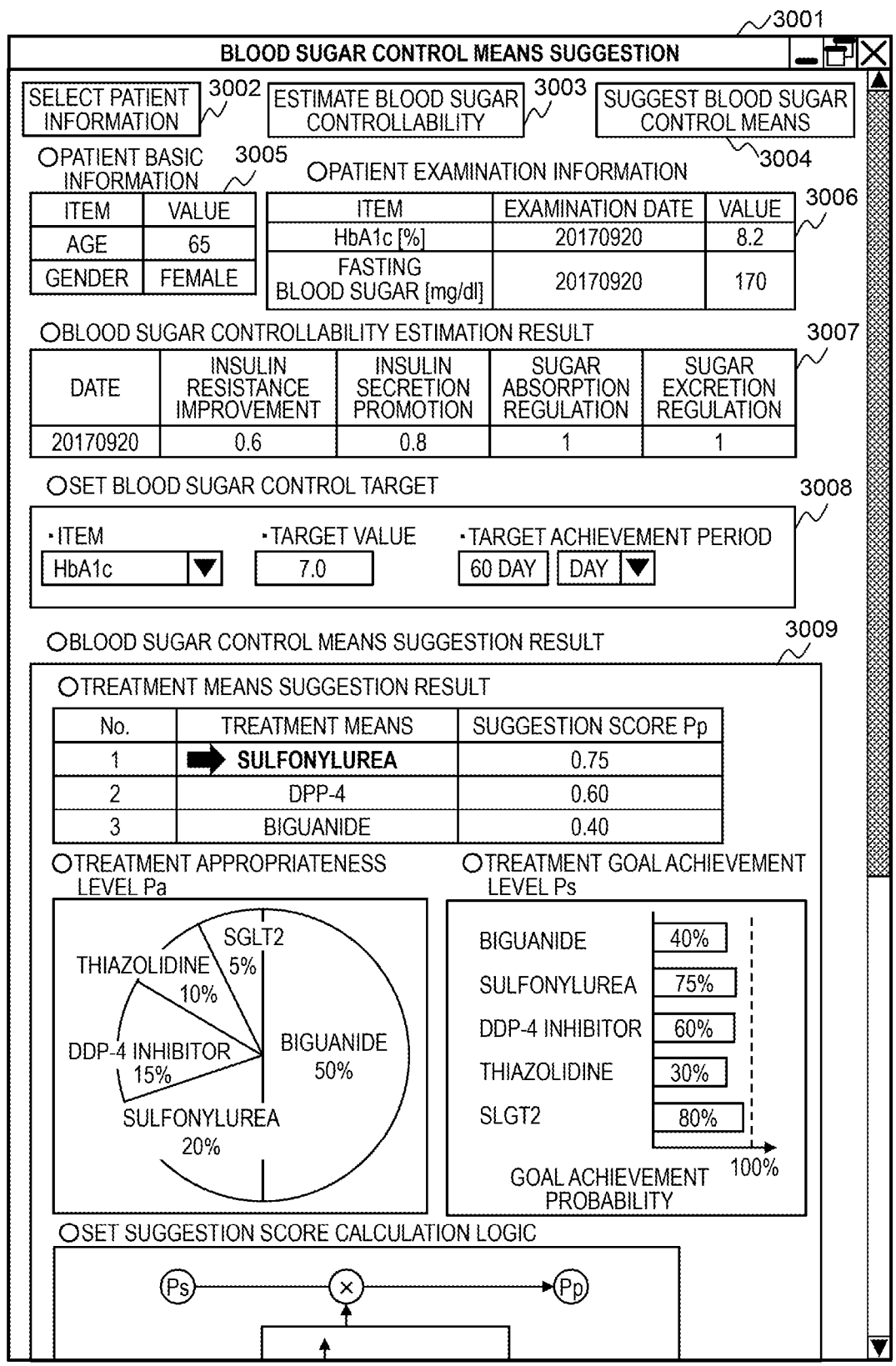

FIG. 16A and FIG. 16B are diagrams for illustrating a user interface screen 3001 according to the first embodiment. Examples of a blood sugar control means suggestion screen illustrated in FIG. 16A and FIG. 16B are an example of the screen 3001 to be displayed on the output unit 1603, and an example of a screen for presenting results of analyzing the blood sugar control means to be suggested for the patient. The screen 3001 includes a patient information selection button 3002, a blood sugar controllability estimation button 3003, a blood sugar control means suggestion button 3004, a patient basic information display area 3005, a patient examination information display area 3006, a blood sugar controllability estimation result display area 3007, a blood sugar control target setting area 3008, and a blood sugar control means suggestion result display area 3009.

The patient information selection button 3002 is a button to be operated to acquire the information on a patient to be analyzed from a database.

The blood sugar controllability estimation button 3003 is a button to be operated to estimate the blood sugar controllability for the patient to be analyzed.

The blood sugar control means suggestion button 3004 is a button to be operated to execute suggestion processing for the blood sugar control means based on the information on the selected patient.

The patient basic information display area 3005 is an area for displaying the basic information on the selected patient.

The patient examination information display area 3006 is an area for displaying the examination information on the selected patient.

The blood sugar controllability estimation result display area 3007 is an area for displaying a result of estimating the blood sugar controllability for the selected patient.

The blood sugar control target setting area 3008 is an area for setting the target of the blood sugar control. The blood sugar control target setting area 3008 includes, for example, a field for designating the item to be subjected to the blood sugar control, a field for setting the target value, and a field for setting the length and the unit of a target achievement period.

The blood sugar control means suggestion result display area 3009 is an area for displaying the blood sugar control means suggestion result. The blood sugar control means suggestion result display area 3009 displays, for example, a processing result obtained by the blood sugar control target achievement level prediction module 1613, a processing result obtained by the blood sugar control means appropriateness level calculation module 1614, and a processing result obtained by the blood sugar control means suggestion module 1612 so as to be visualized in units of blood sugar control means. For example, the goal achievement probability, the blood sugar control means appropriateness level, a suggestion score, and other such indices calculated in units of blood sugar control means may be visualized through representation of a pie chart, a bar chart, and other such graphs. In addition, the information on the blood sugar control means to be suggested is displayed.

The blood sugar control means suggestion result display area 3009 further includes an interface for designating a suggestion score calculation logic being a method of calculating the suggestion score based on the blood sugar control means appropriateness level and the blood sugar control target achievement level. In FIG. 16A, only an area of an upper part of the blood sugar control means suggestion result display area 3009 is illustrated (a lower part of a suggestion score calculation logic setting area is not displayed). In FIG. 16B, a state in which the blood sugar control means suggestion result display area 3009 is entirely displayed through the operation of a scrollbar on the right of the screen 3001 is illustrated.

For example, in the example illustrated in FIG. 16A and FIG. 16B, a method of calculating the suggestion score for the blood sugar control by multiplying the blood sugar control target achievement level by a weight based on a step function relating to the appropriateness level is designated in the blood sugar control means suggestion result display area 3009. In this case, the value of the score of a blood sugar control method having the blood sugar control means appropriateness level equal to or smaller than 0.1 becomes 0, and the value of the score of the blood sugar control method having the blood sugar control means appropriateness level larger than 0.1 becomes the value of the goal achievement probability. With this configuration, the blood sugar control having a higher target achievement level can be preferentially suggested from among the blood sugar control means having a higher appropriateness level than the blood sugar control means having a lower appropriateness level.

The user can confirm the basic information and the examination information on each patient by referring to the screen 3001, and can further assign appropriate blood sugar control means to the patient in consideration of both the probability of achieving the set blood sugar control target and the appropriateness level for the patient.

Figure 17:
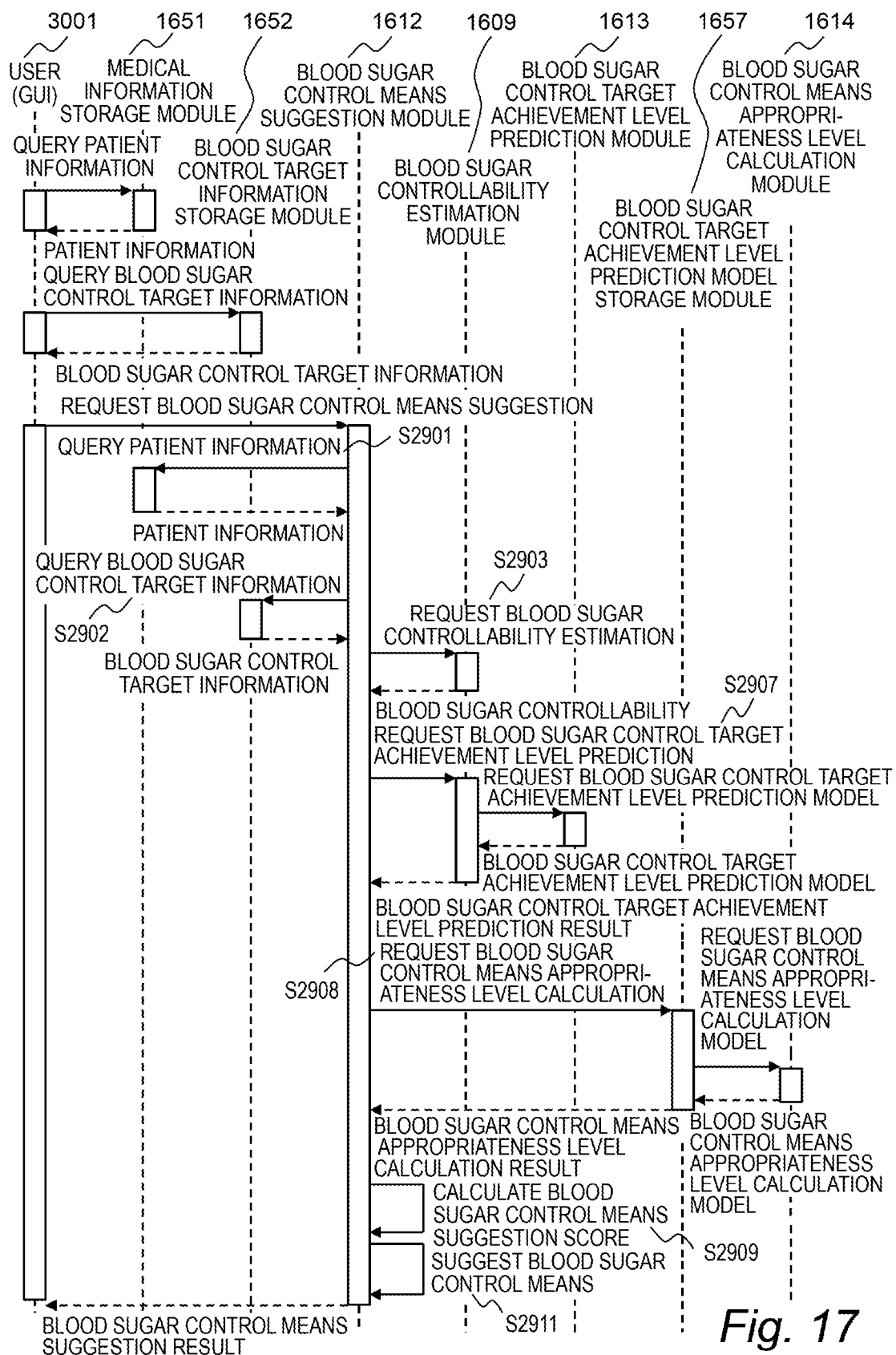
FIG. 17 is a sequence diagram of blood sugar control means suggestion processing according to the first embodiment.

FIG. 17 is a sequence diagram of blood sugar control means suggestion processing using the user interface screen 3001 illustrated in FIG. 16A and FIG. 16B. In this example, the exchange of information and the flow of processing among the user interface screen 3001, the medical information storage module 1651, the blood sugar control target information storage module 1652, the blood sugar control means suggestion module 1612, the blood sugar controllability estimation module 1609, the blood sugar control target achievement level prediction module 1613, the blood sugar control target achievement level prediction model storage module 1657, and the blood sugar control means appropriateness level calculation module 1614 are illustrated. In FIG. 17, reference symbols S2901, S2902, S2903, S2907, S2908, S2909, and S2911 represent the processing steps included in the flow chart illustrated in FIG. 15.

First, the user inputs the information (for example, patient ID or name) on the patient to be analyzed to the input unit 1602, and operates the patient information selection button 3002 to acquire the information on the patient to be analyzed from the medical information storage module 1651. Then, blood sugar control target information on the relevant patient may be acquired from the blood sugar control target information storage module 1652. When the blood sugar control target information on the relevant patient is not set in the blood sugar control target information storage module 1652, the blood sugar control target information input screen may be displayed to prompt the user to input the blood sugar control target information on the relevant patient.

After that, the user operates the blood sugar control means suggestion button 3004 to start the blood sugar control means suggestion processing. The subsequent processing steps are the same as those described with reference to FIG. 15.

As described above, in the treatment selection support system according to the first embodiment, in the treatment of diabetes, it is possible to assign the treatment means that does not deviate from the past diagnosis-and-treatment results and has a high treatment goal achievement level with respect to the blood sugar control target for each patient while taking into consideration the reduction in effect of the drug involved the continuous treatment.

Second Embodiment

The first embodiment has been described by taking an example of the treatment selection support system capable of selecting the blood sugar control means that does not deviate from the past diagnosis-and-treatment results and has the highest blood sugar control target achievement level with respect to the blood sugar control target set for each patient. In the second embodiment, a description is given of a treatment selection support system capable of automatically determining the blood sugar control target appropriate for each patient based on the information on the patient.

The treatment selection support system according to the second embodiment has the same configuration as that illustrated in FIG. 1. The treatment selection support system according to the second embodiment is different from the above-mentioned treatment selection support system according to the first embodiment in that the blood sugar control target suggestion module 1615 functions. The other components and the other processing steps are the same as those in the first embodiment, and hence descriptions thereof are omitted.

The blood sugar control target suggestion module 1615 selects the appropriate blood sugar control target from the blood sugar control target information storage module 1652 based on the information on the patient.

Figure 18:
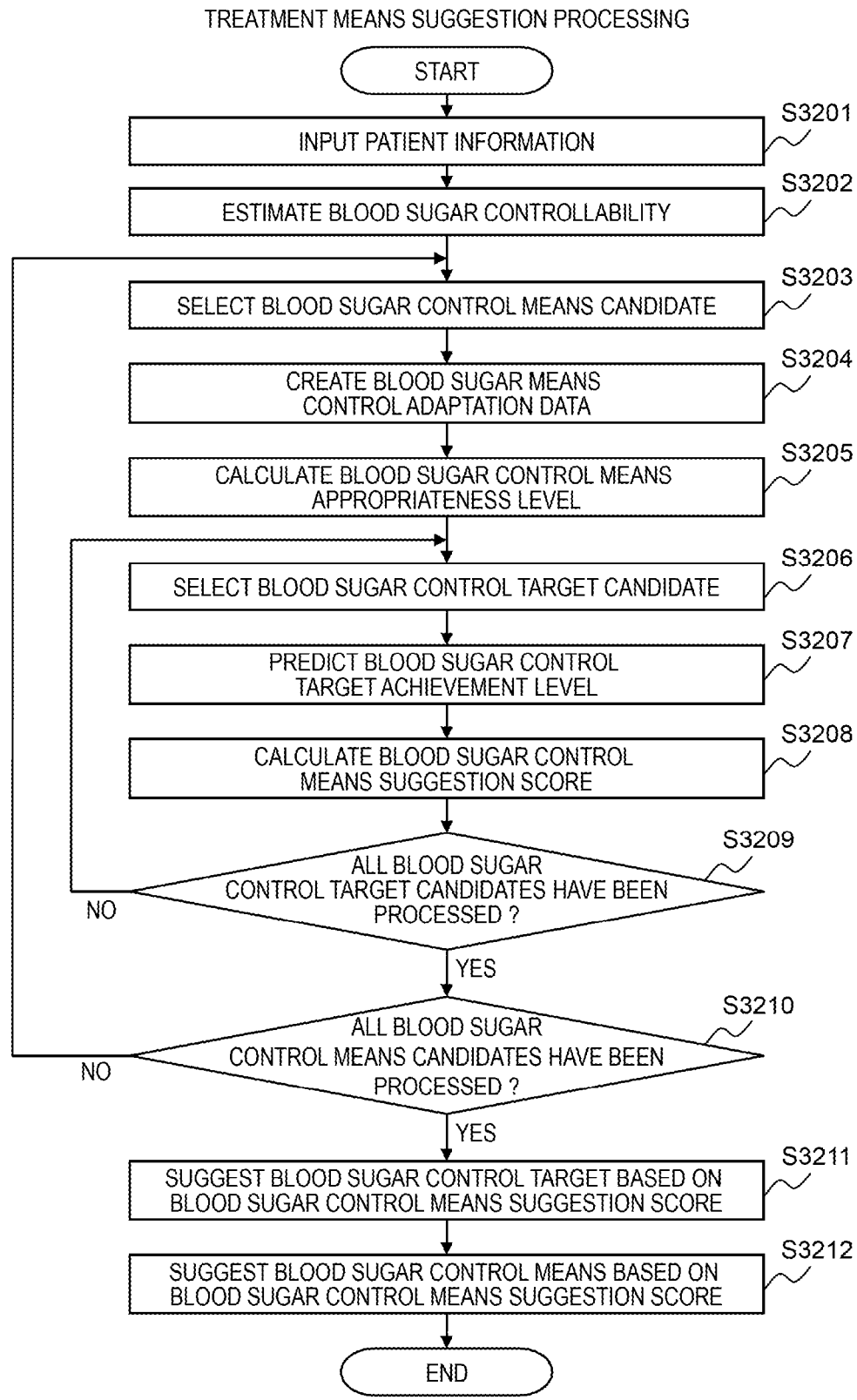
FIG. 18 is a flow chart of processing to be executed by the blood sugar control means suggestion module according to a second embodiment.

FIG. 18 is a flow chart of processing to be executed by the blood sugar control means suggestion module 1612 in the second embodiment. Now, respective processing steps thereof are described.

In Step S3201, the patient basic information 201 on the patient for which the blood sugar control means is to be suggested is input to the blood sugar control means suggestion module 1612. The information to be input includes the examination information 1701 including the age and the gender, the disease information 1801 obtained in the past, and the blood sugar control means implementation information 1901. At this time, the input information is formatted in the same format as that of the formatted information 2301 stored in the formatted information storage module 1655, and is stored in the memory 1605.

In Step S3202, the blood sugar controllability for the subject patient is estimated based on the formatted information formatted in Step S3201. Specifically, the blood sugar controllability estimation scheme to be applied to the subject patient is selected from among the blood sugar controllability estimation schemes 2606 in the blood sugar controllability information 2601 stored in the blood sugar controllability information storage module 1656, and the blood sugar controllability is estimated by the same method as that used for estimating relevant blood sugar controllability information. As the estimation scheme for the blood sugar controllability, a predetermined estimation scheme may be used, or a method appropriate for each individual patient may be designated by the user.

In Step S3203, the blood sugar control means suggestion module 1612 selects one blood sugar control means from the candidates for the blood sugar control means. For example, the blood sugar control means may be supplied as a set of some specific drug names, or may be supplied as the granularity of the category for organizing similar drugs.

In Step S3204, the blood sugar control means suggestion module 1612 creates virtual means adaptation data to be obtained when the blood sugar control means is applied to the patient. Specifically, the information on the predicted blood sugar control means is virtually stored in the blood sugar control means implementation information 2304 in the formatted information 2301, and a record indicating a scenario to be used when the blood sugar control means is implemented is created.

In Step S3205, the blood sugar control means appropriateness level calculation module 1614 uses the blood sugar control means appropriateness level calculation model stored in the blood sugar control means appropriateness level calculation model storage module 1658 to calculate the appropriateness level of the blood sugar control means based on the virtual means adaptation data created in Step S3204.

In Step S3206, the blood sugar control target suggestion module 1615 selects one piece of information to be used as a candidate for the blood sugar control target. For example, the candidate may be selected from among the blood sugar control targets included in the blood sugar control target information 2001 stored in the blood sugar control target information storage module 1652. In this selection, for example, a target having a different blood sugar control target value within a given target achievement period may be selected as the candidate, or a target having a different blood sugar control target achievement period within a range of a given blood sugar control target value may be selected as the candidate.

In Step S3207, the blood sugar control target achievement level prediction module 1613 predicts the target achievement level to be exhibited when the blood sugar control means is applied based on the virtual means adaptation data created in Step S3204. Specifically, the blood sugar control target achievement level prediction module 1613 predicts the target achievement level of the relevant blood sugar control means through use of the blood sugar control target achievement level prediction model corresponding to the blood sugar control target selected in Step S3206 among blood sugar control target achievement level prediction models stored in the blood sugar control target achievement level prediction model storage module 1657.

In Step S3208, the blood sugar control means suggestion module 1612 calculates the blood sugar control means suggestion score of the blood sugar control means to be predicted. The blood sugar control means suggestion score is calculated based on the two indices of the blood sugar control means appropriateness level calculated in Step S3205 and the target achievement level predicted in Step S3207.

Some examples of a method of calculating the blood sugar control means suggestion score are described. In the second embodiment, any method may be employed depending on the characteristics of the target. The first method is a method involving setting a result of one of the four fundamental arithmetic operations between the goal achievement probability and the appropriateness level as a new score. For example, a product of the two indices can be set as the new score. The second method is a method involving defining an activation function based on the appropriateness level, and calculating the blood sugar control means suggestion score by multiplying the value of the defined activation function by the goal achievement probability. For example, such an activation function as to return 0 when the appropriateness level is equal to or smaller than a threshold value and return the value of the appropriateness level itself when the appropriateness level is larger than the threshold value is defined. With this definition, when the appropriateness level is equal to or smaller than a given threshold value, 0 is set as the blood sugar control means suggestion score, and otherwise the product of the two indices is set as the score.

In Step S3209, the blood sugar control means suggestion module 1612 determines whether or not the blood sugar control means suggestion score has been calculated for all the candidates for the blood sugar control target. When the calculation of the blood sugar control means suggestion score has been finished for all the candidates for the blood sugar control target, the procedure advances to Step S3210. Meanwhile, when the calculation of the blood sugar control means suggestion score has not been finished for a part of the candidates for the blood sugar control means, the procedure advances to Step S3206. In Step S3209, the candidates for the blood sugar control target for which it is to be determined whether or not the calculation of the blood sugar control means suggestion score has been finished may be, for example, all the blood sugar control targets included in the blood sugar control target information 2001 stored in the blood sugar control target information storage module 1652. Further, the candidates may be the blood sugar control targets within a given blood sugar control target achievement period, or may be the blood sugar control targets within a range of a given blood sugar control target.

In Step S3210, the blood sugar control means suggestion module 1612 determines whether or not the blood sugar control means suggestion scores of all the candidates for the blood sugar control means have been calculated. When the calculation of the blood sugar control means suggestion scores of all the candidates for the blood sugar control means has been finished, the procedure advances to Step S3211. Meanwhile, when the calculation of the blood sugar control means suggestion scores of a part of the candidates for the blood sugar control means has not been finished, the procedure advances to Step S3203.

In Step S3211, the blood sugar control means suggestion module 1612 suggests the blood sugar control target based on the information on the blood sugar control means suggestion score calculated for each blood sugar control target candidate and each blood sugar control means.

Some examples of a method of suggesting the treatment means are described. In the second embodiment, any method may be employed. A first method is a method involving suggesting, as the blood sugar control target for the patient, the blood sugar control target for which the highest value has been calculated for the blood sugar control means suggestion score. With the first method, it is possible to suggest the blood sugar control target highly expected to be achieved by the treatment (blood sugar control) that does not deviate from the actual diagnosis-and-treatment results. A second method is a method involving suggesting the blood sugar control target having at least one blood sugar control means having the blood sugar control means suggestion score equal to or larger than a threshold value. With the second method, it is possible to perform the suggestion by excluding the treatment goal (blood sugar control target) less likely to be achieved. The two examples are described above, but a method of suggesting the blood sugar control target is not limited to the methods taken as examples. Various methods can be employed when the suggestion is performed by utilizing the blood sugar control means suggestion score calculated for each blood sugar control target and each blood sugar control means.

In Step S3212, the blood sugar control means suggestion module 1612 suggests appropriate blood sugar control means based on the blood sugar control means suggestion score calculated for each blood sugar control means.

Some examples of a method of suggesting the blood sugar control means are described. In the second embodiment, any method may be employed. A first method is a method involving suggesting the blood sugar control means having the maximum blood sugar control means suggestion score among the blood sugar control means for the blood sugar control target suggested in Step S3208. A second method is a method involving suggesting at least one blood sugar control means having the blood sugar control means suggestion score equal to or larger than a threshold value among the blood sugar control means for the blood sugar control target suggested in Step S3208. The suggested blood sugar control means is, for example, presented to the user by the output unit 1603.

As described above, in the treatment selection support system according to the second embodiment, the blood sugar control target appropriate for each patient can be automatically determined based on the information on the patient.

In the treatment selection support system according to the second embodiment, in addition to the effects described at the beginning, it is possible to suggest the blood sugar control target for each patient. For example, when a given blood sugar control target is set for the patient but is hardly expected to be achieved through use of any blood sugar control means, it is highly probable that the blood sugar control target is a target that is difficult for the patient to achieve. In the treatment selection support system according to the second embodiment, the blood sugar control means suggestion score is calculated for each blood sugar control target and each blood sugar control means, and the blood sugar control target is determined through use of the blood sugar control means suggestion score, to thereby provide the user with, for example, information on the blood sugar control target having a high probability of achievement.

The first embodiment and the second embodiment have been described by taking means for treating diabetes (blood sugar control means) as an example, but in a more general sense, this invention can also be applied to symptomatic treatment of another chronic disease. In this case, in each of the components and processing steps in the first embodiment and the second embodiment, the "blood sugar control" is paraphrased as "treatment". For example, this invention can also be applied to the treatment of hypertension, mental disorder (depression), dementia, and cancer with an anti-cancer agent. In particular, with a disease involving a plurality of organs, the organ in which efficacy is exhibited differs depending on the treatment means. Therefore, it is possible to suggest more appropriate treatment means in consideration of action mechanism information.

As described above, according to the embodiments of this invention, the data analysis module 1601 includes: the blood sugar control target achievement determination module 1607 configured to create the blood sugar control target achievement determination information 2201 including an achievement level of the blood sugar control target for each blood sugar control means based on the formatted information 2301; the blood sugar controllability estimation module 1609 configured to create the blood sugar controllability information 2601 including a history of implementing the blood sugar control means for each action mechanism category; the blood sugar control target achievement level prediction model creation module 1610 configured to create the blood sugar control target achievement level prediction model for predicting the achievement level of the blood sugar control target based on the formatted information 2301, the blood sugar control target achievement determination information 2201, and the blood sugar controllability information 2601; the blood sugar control means appropriateness level calculation model creation module 1611 configured to create the blood sugar control means appropriateness level calculation model for calculating the appropriateness level of the blood sugar control means based on the formatted information 2301, the blood sugar control target achievement determination information 2201, and the blood sugar controllability information 2601; the blood sugar control target achievement level prediction module 1613 configured to use the blood sugar control target achievement level prediction model to predict the achievement level of the blood sugar control target for the patient for each blood sugar control means; the blood sugar control means appropriateness level calculation module 1614 configured to use the blood sugar control means appropriateness level calculation model to calculate the appropriateness level of the blood sugar control means for the patient; and the blood sugar control means suggestion module 1612 configured to provide the information on the blood sugar control means appropriate for the patient based on the predicted blood sugar control target achievement level and the calculated blood sugar control means appropriateness level. Therefore, it is possible to select the blood sugar control means that does not deviate from the past diagnosis-and-treatment results and has a high blood sugar control target achievement level with respect to the blood sugar control target set for each patient. Further, it is possible to assign the blood sugar control means that does not deviate from the past diagnosis-and-treatment results and has a high blood sugar control target achievement level to the blood sugar control target set for each patient while taking into consideration the reduction in effect involved in the continuous treatment for each drug action mechanism.

Further, the blood sugar controllability estimation module 1609 creates a relationship model indicating a relationship between the implementation of the blood sugar control means included in the formatted information for each action mechanism category and the result obtained by the blood sugar control means, uses the relationship model to predict the result obtained by the blood sugar control means, and creates the blood sugar controllability information 2601 including the predicted result or information on a parameter used for predicting the result, to thereby be able to assign the blood sugar control means that does not deviate from the past diagnosis-and-treatment results and has a high blood sugar control target achievement level in consideration of the long-term treatment history.

Further, the blood sugar control target achievement determination module 1607 determines the achievement level of the blood sugar control target based on whether or not the blood sugar control target was successfully achieved, the blood sugar control target achievement level prediction model creation module 1610 creates the blood sugar control target achievement level prediction model for predicting an achievement probability of the blood sugar control target based on the formatted information 2301, the blood sugar control target achievement determination information 2201, and the blood sugar controllability information 2601, and the blood sugar control target achievement level prediction module 1613 predicts the achievement probability of the blood sugar control target as the blood sugar control target achievement level for each blood sugar control means. Therefore, the user can use the probability easy to understand as the index to predict the achievement probability of the blood sugar control target.

Further, the blood sugar control means appropriateness level calculation model creation module 1611 creates the blood sugar control means appropriateness level calculation model for predicting the probability that the blood sugar control means is assigned to the patient based on the formatted information 2301, the blood sugar control target achievement determination information 2201, and the blood sugar controllability information 2601, and the blood sugar control means appropriateness level calculation module 1614 predicts the probability that the relevant blood sugar control means is assigned to the patient as the blood sugar control means appropriateness level for each blood sugar control means. Therefore, the user can use the probability easy to understand as the index to predict the appropriateness level of the blood sugar control means.

Further, the blood sugar control means suggestion module 1612 provides the information on the blood sugar control means appropriate for the patient based on the suggestion score calculated by assigning a weight of the value of the blood sugar control means appropriateness level to the value of the blood sugar control target achievement level. Therefore, the effectiveness of the blood sugar control means can be quantitatively grasped by the suggestion score, and the information on the blood sugar control means can be provided with accuracy.

Further, the data analysis module 1601 includes the blood sugar control target suggestion module 1615 configured to provide the information on the blood sugar control target appropriate for the patient based on the blood sugar control target achievement level and the blood sugar control means appropriateness level. Therefore, it is possible to determine the blood sugar control target appropriate (for example, high in achievement probability) for each patient.

Representative aspects of this invention other than those described in the appended claims include the following.

(1) A treatment selection support system, which is configured to support selection of treatment means, the treatment selection support system including a computer including:
an arithmetic unit configured to execute predetermined processing;
a storage device coupled to the arithmetic unit; and
a communication interface coupled to the arithmetic unit,
the storage device being configured to store formatted information including information on the treatment performed on a patient;
the treatment selection support system including:
a target achievement determination module configured to create target achievement determination information including an achievement level of a treatment target for each treatment means based on the formatted information;
an achievement level prediction model creation module configured to create an achievement level prediction model for predicting the achievement level of the treatment target based on the formatted information and the target achievement determination information;
an appropriateness level calculation model creation module configured to create an appropriateness level calculation model for calculating an appropriateness level of the treatment means based on the formatted information and the target achievement determination information;
an achievement level prediction module configured to use the achievement level prediction model to predict the achievement level of the treatment target for the patient for each treatment means;
an appropriateness level calculation module configured to use the appropriateness level calculation model to calculate the appropriateness level of the treatment means for the patient; and
a treatment means suggestion module configured to provide information on the treatment means appropriate for the patient based on the predicted achievement level and the calculated appropriateness level.

(2) The treatment selection support system,
in which the target achievement determination module is configured to determine the achievement level of the treatment target based on whether the treatment target has been successfully achieved,
in which the achievement level prediction model creation module is configured to create an achievement level prediction model for predicting an achievement probability of the treatment target based on the formatted information and the target achievement determination information, and
in which the achievement level prediction module is configured to predict the achievement probability of the treatment target as the achievement level of the treatment target for each treatment means.

(3) The treatment selection support system,
in which the appropriateness level calculation model creation module is configured to create the appropriateness level calculation model for predicting a probability that the relevant treatment means is assigned to the patient based on the formatted information and the target achievement determination information, and
in which the appropriateness level calculation module is configured to predict the probability that the treatment means is assigned to the patient as the appropriateness level of the treatment means for each treatment means.

(4) The treatment selection support system, in which the treatment means suggestion module is configured to provide the information on the treatment means appropriate for the patient based on a suggestion score calculated by assigning a weight of a value of the appropriateness level to a value of the achievement level.

(5) The treatment selection support system, further including a treatment target suggestion module configured to provide the information on the treatment target appropriate for the patient based on the achievement level and the appropriateness level.

(6) The treatment selection support system,
in which the storage device is configured to store action mechanism information in which the treatment means and an action mechanism category are associated with each other,
in which the treatment selection support system further includes a treatment efficacy estimation module configured to create treatment efficacy information including a history of implementing the treatment means for each action mechanism category,
in which the achievement level prediction model creation module is configured to create the achievement level prediction model based on the formatted information, the target achievement determination information, and the treatment efficacy information, and
in which the appropriateness level calculation model creation module is configured to create the appropriateness level calculation model based on the formatted information, the target achievement determination information, and the treatment efficacy information.

(7) The treatment selection support system, in which the treatment efficacy estimation module is configured to:
create a relationship model indicating a relationship between implementation of the treatment means included in the formatted information for each action mechanism category and a result to be obtained by the treatment means;
use the relationship model to predict a treatment result for each timing at which the treatment means is assigned; and
create treatment efficacy information including one of the predicted treatment result and information on a parameter used for predicting the treatment result.

(8) A method of supporting selection of treatment means by a treatment selection support system, the treatment selection support system including a computer including:
an arithmetic unit configured to execute predetermined processing;
a storage device coupled to the arithmetic unit; and
a communication interface coupled to the arithmetic unit,
the storage device being configured to store formatted information including information on the treatment performed on a patient;
the method including:
a target achievement determination step of creating, by the arithmetic device, target achievement determination information including an achievement level of a treatment target for each treatment means based on the formatted information;

an achievement level prediction model creation step of creating, by the arithmetic device, an achievement level prediction model for predicting the achievement level of the treatment target based on the formatted information and the target achievement determination information;

an appropriateness level calculation model creation step of creating, by the arithmetic device, an appropriateness level calculation model for calculating an appropriateness level of the treatment means based on the formatted information and the target achievement determination information;

an achievement level prediction step of using, by the arithmetic device, the achievement level prediction model to predict the achievement level of the treatment target for the patient for each treatment means;

an appropriateness level calculation step of using, by the arithmetic device, the appropriateness level calculation model to calculate the appropriateness level of the treatment means for the patient; and a treatment means suggestion step of providing, by the arithmetic device, information on the treatment means appropriate for the patient based on the predicted achievement level and the calculated appropriateness level.

This invention is not limited to the above-described embodiments but includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, processing modules, and processing means, for all or a part of them, may be implemented by hardware: for example, by designing an integrated circuit, and may be implemented by software, which means that a processor interprets and executes programs providing the functions.

The information of programs, tables, and files to implement the functions may be stored in a storage device such as a memory, a hard disk drive, or an SSD (a Solid State Drive), or a storage medium such as an IC card, or an SD card.

The drawings illustrate control lines and information lines as considered necessary for explanation but do not illustrate all control lines or information lines in the products. It can be considered that almost of all components are actually interconnected.

What is claimed is:

1. A treatment selection support system, which is configured to support selection of a blood sugar control drug from a plurality of blood sugar control drugs for treatment of diabetes, the treatment selection support system including a computer including:
   at least one processor configured to execute predetermined processing;
   a storage device coupled to the at least one processor; and
   a communication interface coupled to the at least one processor, the storage device being configured to store:
   drug action mechanism information in which each of the plurality of blood sugar control drugs is associated with a drug action mechanism category, the drug action mechanism category including at least sugar absorption regulation, sugar excretion regulation, insulin secretion promotion, and insulin resistance improvement; and
   formatted information including information on the treatment performed on a patient, the at least one processor configured to execute the predetermined processing to:
   create target achievement determination information including an achievement level of a blood sugar control target for each of the plurality of blood sugar control drugs based on the formatted information;
   create blood sugar controllability information including a history of implementing each of the plurality of blood sugar control drugs for each drug action mechanism category;
   create an achievement level prediction model for predicting the achievement level of the blood sugar control target based on the formatted information, the target achievement determination information, and the blood sugar controllability information;
   create an appropriateness level calculation model for calculating an appropriateness level of each of the plurality of blood sugar control drugs based on the formatted information, the target achievement determination information, and the blood sugar controllability information;
   use the achievement level prediction model to predict the achievement level of the blood sugar control target for the patient for each of the plurality of blood sugar control drugs;
   use the appropriateness level calculation model to calculate the appropriateness level of each of the plurality of blood sugar control drugs for the patient; and
   provide information on each of the plurality of blood sugar control drugs appropriate for the patient based on the predicted achievement level and the calculated appropriateness level,
   wherein the provided information on each of the plurality of blood sugar control drugs comprises a suggestion score calculated for each of the plurality of blood sugar control drugs for the patient,
   wherein the suggestion score is calculated by multiplying a value of the predicted achievement level, of each of the plurality of blood sugar control drugs, by a weight,
   wherein the weight is based on a value of the calculated appropriateness level of each of the plurality of blood sugar control drugs,
   wherein the plurality of blood sugar control drugs are ranked according to the suggestion scores, and
   wherein treatment of diabetes for the patient is executed based on the ranking and the suggestion scores for the plurality of blood sugar control drugs.

2. The treatment selection support system according to claim 1, wherein the at least one processor is configured to execute the predetermined processing to:
   create a relationship model indicating a relationship between implementation of each of the plurality of blood sugar control drugs included in the formatted information for each drug action mechanism category and a result to be obtained by each of the plurality of blood sugar control drugs;
   use the relationship model to predict the result to be obtained by each of the plurality of blood sugar control drugs; and
   create the blood sugar controllability information including one of the predicted result and information on a parameter used for predicting the result.

3. The treatment selection support system according to claim 1, wherein the at least one processor is configured to execute the predetermined processing to:
   determine the achievement level of the blood sugar control target based on whether the blood sugar control target has been successfully achieved,
   create an achievement level prediction model for predicting an achievement probability of the blood sugar control target based on the formatted information, the target achievement determination information, and the blood sugar controllability information, and
   predict the achievement probability of the blood sugar control target as the achievement level of the blood sugar control target for each of the plurality of blood sugar control drugs.

4. The treatment selection support system according to claim 1, wherein the at least one processor is configured to execute the predetermined processing to:
   create the appropriateness level calculation model for predicting a probability that the a relevant blood sugar control drug, of the plurality of blood sugar control drugs, is assigned to the patient based on the formatted information, the target achievement determination information, and the blood sugar controllability information, and
   predict the probability that the relevant blood sugar control drug is assigned to the patient as the appropriateness level for each of the plurality of blood sugar control drugs.

5. The treatment selection support system according to claim 1, wherein the at least one processor is configured to execute the predetermined processing to provide the information on the blood sugar control target appropriate for the patient based on the achievement level and the appropriateness level.

6. A method of supporting selection of a blood sugar control drug from a plurality of blood sugar control drugs for treatment of diabetes by a treatment selection support system, the treatment selection support system including a computer,
   the computer including at least one processor configured to execute predetermined processing, a storage device coupled to the at least one processor, and a communication interface coupled to the at least one processor,
   the storage device being configured to store drug action mechanism information in which each of the plurality of blood sugar control drugs is associated with an a drug action mechanism category, the drug action mechanism category including at least sugar absorption regulation, sugar excretion regulation, insulin secretion promotion, and insulin resistance improvement, and formatted information including information on the treatment performed on a patient,
   the method including:
      a target achievement determination step of creating, by the at least one processor, target achievement determination information including an achievement level of a blood sugar control target for each of the plurality of blood sugar control drugs based on the formatted information;
      a blood sugar controllability estimation step of creating, by the at least one processor, blood sugar controllability information including a history of implementing each of the plurality of blood sugar control drugs for each drug action mechanism category;
      an achievement level prediction model creation step of creating, by the at least one processor, an achievement level prediction model for predicting the achievement level of the blood sugar control target based on the formatted information, the target achievement determination information, and the blood sugar controllability information;
      an appropriateness level calculation model creating step of creating, by the at least one processor, an appropriateness level calculation model for calculating an appropriateness level of each of the plurality of blood sugar control drugs based on the formatted information, the target achievement determination information, and the blood sugar controllability information;
      an achievement level prediction step of using, by the at least one processor, the achievement level prediction model to predict the achievement level of the blood sugar control target for the patient for each of the plurality of blood sugar control drugs;
      an appropriateness level calculation step of using, by the at least one processor, the appropriateness level calculation model to calculate the appropriateness level of each of the plurality of blood sugar control drugs for the patient; and
      a blood sugar control drug suggestion step of providing, by the at least one processor, information on each of the plurality of blood sugar control drugs appropriate for the patient based on the predicted achievement level and the calculated appropriateness level, wherein the provided information on each of the plurality of blood sugar control drugs comprises a suggestion score calculated for each of the plurality of blood sugar control drugs for the patient,
      wherein the suggestion score is calculated by multiplying a value of the predicted achievement level, of each of the plurality of blood sugar control drugs, by a weight,
      wherein the weight is based on a value of the calculated appropriateness level of each of the plurality of blood sugar control drugs,
      wherein the plurality of blood sugar control drugs are ranked according to the suggestion scores, and
      wherein treatment of diabetes for the patient is executed based on the ranking and the suggestion scores for the plurality of blood sugar control drugs.

7. The method according to claim 6, wherein the blood sugar controllability estimation step comprises:
   creating, by the at least one processor, a relationship model indicating a relationship between implementation of each of the plurality of blood sugar control drugs included in the formatted information for each action mechanism category and a result to be obtained by each of the plurality of blood sugar control drugs;
   using, by the at least one processor, the relationship model to predict the result to be obtained by each of the plurality of blood sugar control drugs; and
   creating, by the at least one processor, the blood sugar controllability information including one of the predicted result and information on a parameter used for predicting the result.

8. The method according to claim 6,
   wherein the target achievement determination step comprises determining, by the at least one processor, the achievement level of the blood sugar control target based on whether the blood sugar control target has been successfully achieved,
   wherein the achievement level prediction model creation step comprises creating, by the at least one processor, an achievement level prediction model for predicting an achievement probability of the blood sugar control target based on the formatted information and the target achievement determination information, and wherein the achievement level prediction step comprises predicting, by the at least one processor, the achievement probability of the blood sugar control target as the achievement level of the blood sugar control target for each of the plurality of blood sugar control drugs.

9. The method according to claim 6, wherein the appropriateness level calculation model creation step comprises creating, by the at least one processor, the appropriateness level calculation model for predicting a probability that a relevant blood sugar control drug, of the plurality of blood sugar control drugs, is assigned to the patient based on the formatted information and the target achievement determination information, and wherein the appropriateness level calculation step comprises predicting, by the at least one processor, the probability that the relevant blood sugar control drug is assigned to the patient as the appropriateness level for each of the plurality of blood sugar control drugs.

10. The method according to claim 6, further comprising a blood sugar control target suggestion step of providing, by the at least one processor, the information on the blood sugar control target appropriate for the patient based on the achievement level and the appropriateness level.

11. A treatment selection support system, which is configured to support selection of a blood sugar control drug from a plurality of blood sugar control drugs for treatment of diabetes, the treatment selection support system including a computer, the computer including at least one processor configured to execute predetermined processing, a storage device coupled to the at least one processor, and a communication interface coupled to the at least one processor, the storage device being configured to store formatted information including information on the treatment performed on a patient the at least one processor configured to execute the predetermined processing to:

create target achievement determination information including an achievement level of a blood sugar control target for each of the plurality of blood sugar control drugs based on the formatted information;

create an achievement level prediction model for predicting the achievement level of the blood sugar control target based on the formatted information and the target achievement determination information;

create an appropriateness level calculation model for calculating an appropriateness level of each of the plurality of blood sugar control drugs based on the formatted information and the target achievement determination information;

use the achievement level prediction model to predict the achievement level of the blood sugar control target for the patient for each of the plurality of blood sugar control drugs;

use the appropriateness level calculation model to calculate the appropriateness level of each of the plurality of blood sugar control drugs for the patient; and provide information on each of the plurality of blood sugar control drugs appropriate for the patient based on the predicted achievement level and the calculated appropriateness level, wherein the provided information on each of the plurality of blood sugar control drugs comprises a suggestion score calculated for each of the plurality of blood sugar control drugs for the patient, wherein the suggestion score is calculated by multiplying a value of the predicted achievement level, of each of the plurality of blood sugar control drugs, by a weight, wherein the weight is based on a value of the calculated appropriateness level of each of the plurality of blood sugar control drugs, wherein the plurality of blood sugar control drugs are ranked according to the suggestion scores, and wherein treatment of diabetes for the patient is executed based on the ranking and the suggestion scores for the plurality of blood sugar control drugs.

\* \* \* \* \*